(12) United States Patent
Wu et al.

(10) Patent No.: US 11,623,103 B2
(45) Date of Patent: Apr. 11, 2023

(54) SYSTEMS AND METHODS FOR ENHANCING PLATELET BIOGENESIS AND EXTENDING PLATELET LIFESPAN WITH LOW LEVEL LIGHT

(71) Applicant: THE GENERAL HOSPITAL CORPORATION, Boston, MA (US)

(72) Inventors: Meixiong Wu, Boston, MA (US); Qi Zhang, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 343 days.

(21) Appl. No.: 16/875,111

(22) Filed: May 15, 2020

(65) Prior Publication Data

US 2020/0276449 A1 Sep. 3, 2020

Related U.S. Application Data

(63) Continuation of application No. 15/465,924, filed on Mar. 22, 2017, now abandoned, which is a
(Continued)

(51) Int. Cl.
*A61B 5/06* (2006.01)
*A61N 5/06* (2006.01)
*A61N 5/067* (2006.01)

(52) U.S. Cl.
CPC ......... *A61N 5/0601* (2013.01); *A61N 5/0613* (2013.01); *A61N 5/067* (2021.08);
(Continued)

(58) Field of Classification Search
CPC .... A61N 5/0601; A61N 5/0613; A61N 5/067; A61N 2005/0651; A61N 2005/0659; A61N 2005/0662
(Continued)

(56) References Cited

U.S. PATENT DOCUMENTS 6,063,108 A    5/2000   Salansky et al.
6,395,016 B1 *   5/2002   Oron ........................ A61B 8/12
                                                      128/898
(Continued)

FOREIGN PATENT DOCUMENTS

WO   WO-2007047892 A1 *   4/2007  ........... A61N 5/0613

OTHER PUBLICATIONS

Gao, Xuejuan, and Da Xing. "Molecular mechanisms of cell proliferation induced by low power laser irradiation." Journal of biomedical science 16.1 (2009): 4.
(Continued)

*Primary Examiner* — Carl H Layno
*Assistant Examiner* — Michael J Lau
(74) *Attorney, Agent, or Firm* — Quarles & Brady LLP

(57) ABSTRACT

The present disclosure is directed to systems and methods that can apply low level light (LLL) to facilitate platelet biogenesis or extend platelet lifespan. While not wishing to be bound by theory, it is believed that LLL can enhance the ATP synthesis by the mitochondria within platelets and/or platelet precursor cells, which, thereby, helps to enhance platelet biogenesis and extend the platelet lifespan. In some instances, LLL can facilitate in vitro and/or in vivo platelet biogenesis. In other instances, LLL can extend platelet lifespan in circulation. In still other instances, LLL can be employed to prolong the shelf-life of stored platelets.

18 Claims, 22 Drawing Sheets

Related U.S. Application Data continuation-in-part of application No. PCT/US2015/051323, filed on Sep. 22, 2015.

(60) Provisional application No. 62/054,602, filed on Sep. 24, 2014, provisional application No. 62/443,909, filed on Jan. 9, 2017.

(52) U.S. Cl.
CPC ............... *A61N 2005/0612* (2013.01); *A61N 2005/0651* (2013.01); *A61N 2005/0659* (2013.01); *A61N 2005/0662* (2013.01)

(58) Field of Classification Search
USPC .......................................................... 607/89
See application file for complete search history.

(56) References Cited

U.S. PATENT DOCUMENTS

| | | | |
|---|---|---|---|
| 6,596,016 | B1 | 7/2003 | Vreman et al. |
| 8,182,473 | B2 * | 5/2012 | Altshuler ............ A61B 18/203 606/9 |
| 2003/0125782 | A1 | 7/2003 | Streeter |
| 2004/0111132 | A1 | 6/2004 | Shenderova et al. |
| 2004/0260367 | A1 * | 12/2004 | De Taboada ......... A61N 5/0601 607/88 |
| 2005/0192637 | A1 | 9/2005 | Girouard et al. |
| 2005/0282143 | A1 | 12/2005 | Goodrich et al. |
| 2008/0138791 | A1 | 6/2008 | Stossel et al. |
| 2009/0069872 | A1 | 3/2009 | Fortuna et al. |
| 2010/0292200 | A1 | 11/2010 | Kile et al. |
| 2011/0060266 | A1 | 3/2011 | Streeter et al. |
| 2012/0016174 | A1 * | 1/2012 | De Taboada ............ A61N 5/04 607/3 |
| 2012/0041521 | A1 * | 2/2012 | Oron .................... A61N 5/0613 607/92 |
| 2012/0065712 | A1 | 3/2012 | Rivera et al. |
| 2013/0183354 | A1 | 7/2013 | Harrison, Jr. et al. |
| 2014/0012353 | A1 | 1/2014 | Prescott |
| 2014/0031906 | A1 | 1/2014 | Brezinski |
| 2014/0039581 | A1 | 2/2014 | Oron et al. |
| 2015/0065943 | A1 | 3/2015 | Debow |

OTHER PUBLICATIONS

Eells, Janis T., et al. "Mitochondrial signal transduction in accelerated wound and retinal healing by near-infrared light therapy." Mitochondrion 4.5-6 (2004): 559-567.
International Search Report for Application No. PCT/US15/51323 dated Dec. 15, 2015.

\* cited by examiner

SYSTEMS AND METHODS FOR ENHANCING PLATELET BIOGENESIS AND EXTENDING PLATELET LIFESPAN WITH LOW LEVEL LIGHT

RELATED APPLICATIONS

This application is a continuation of U.S. patent application Ser. No. 15/465,924, filed Mar. 22, 2017, entitled "SYSTEMS AND METHODS FOR ENHANCING PLATELET BIOGENESIS AND EXTENDING PLATELET LIFESPAN, IN CIRCULATION AND IN STORAGE, WITH LOW LEVEL LIGHT," which is a Continuation in Part of Intl Patent Appln. Serial No. PCT/US15/51323, filed Sep. 22, 2015, entitled "SYSTEMS AND METHODS FOR ENHANCING PLATELET BIOGENESIS AND EXTENDING PLATELET LIFESPAN, IN CIRCULATION AND IN STORAGE, WITH LOW LEVEL LIGHT," which claims the benefit of U.S. Provisional Application No. 62/054,602, filed Sep. 24, 2014, entitled "SYSTEMS AND METHODS FOR ENHANCING PLATELET BIOGENESIS AND EXTENDING PLATELET LIFESPAN, IN CIRCULATION AND IN STORAGE, WITH LOW LEVEL LIGHT." The entirety of these applications is hereby incorporated by reference for all purposes.

U.S. patent application Ser. No. 15/465,924 also claims the benefit of U.S. Provisional Application No. 62/443,909, filed Jan. 9, 2017, entitled "SYSTEMS AND METHODS FOR ENHANCING PLATELET BIOGENESIS AND EXTENDING PLATELET LIFESPAN, IN CIRCULATION AND IN STORAGE, WITH LOW LEVEL LIGHT,". The entirety of these applications is hereby incorporated by reference for all purposes.

TECHNICAL FIELD

The present disclosure relates generally to platelet biogenesis and storage and, more specifically, to systems and methods that employ low level light (1) to enhance either in vivo or in vitro platelet biogenesis and/or (2) to extend platelet lifespan in either in vivo circulation or in vitro storage.

BACKGROUND

Platelets are irregular, disc-shaped elements in the blood that assist in blood clotting. An abnormally low level of platelets in the blood is referred to as thrombocytopenia. For example, thrombocytopenia can occur after γ-irradiation exposure, after trauma, after platelet donation, as a side effect of cancer chemotherapy or radiotherapy, or in patients with an inherent deficiency in thrombopoiesis. Patients with thrombocytopenia can exhibit an increased risk of hemorrhage and death due to uncontrollable bleeding. The only effective means to manage thrombocytopenia is platelet transfusion because, although there are several biological agents and drugs that are either FDA-approved (e.g., IL-11) or in clinical trials, the effects of these drugs are modest and cause side effects, particularly with high dosages.

With a rising number of cancer patients undergoing single or multiple cycles of chemotherapy, radiotherapy and/or surgery, the threat of nuclear or radiological terrorism, as well as unpredictable γ-irradiation accidents, such as the Fukushima Daiichi nuclear disaster in 2011, the need for platelet transfusions is fast growing and expected to continue. However, due to increasingly stringent regulations, national blood donation rates are dropping and the platelets that are donated have a relatively short shelf life (limited to only five days by the U.S. Food and Drug Administration (FDA)), so a large number of donated platelet units are discarded every year.

Platelet transfusions are expensive and frequently associated with complications, including transfusion-transmitted diseases, allergic reactions, graft-versus-host reactions, infections, and platelet refractoriness. Accordingly, platelet transfusion is relatively rare, often limited to patients in critical condition, because the benefits of these transfusions must always outweigh the potential risks to the patient. A safe, convenient, and cost-effective modality to augment platelet regeneration in vivo would greatly reduce the need of platelet transfusions and confer primary or secondary prophylaxis of thrombocytopenia.

SUMMARY

The present disclosure relates generally to platelet biogenesis and storage. More specifically, the present disclosure relates to employing low level light (LLL) to facilitate platelet biogenesis, prolong platelet life in circulation and in storage. One aspect of the present disclosure is directed to employing LLL (e.g., alone or in combination with other drugs and/or biological agents) to facilitate both in vitro and in vivo platelet biogenesis. A further aspect of the present disclosure is directed to employing LLL (e.g., alone or in combination with other agents), to prolong the shelf-life of stored platelets and the lifespan of circulating platelets within a patient's blood.

In one aspect, the present disclosure can include a device configured to apply low level light (LLL) to bone marrow, liver, platelets and/or platelet precursors (e.g., megakaryocytes (MKs). For example, the LLL can be used to facilitate platelet biogenesis, prolong platelet life in in vivo circulation, and/or in in vitro platelet storage. The device can include a controller, comprising a non-transitory memory and a processor, that can be configured to generate a control signal comprising a parameter for the LLL application. The device can also include a LLL generator that can be configured to receive the control signal, generate the LLL based on the parameter, and apply the generated LLL to at least one of the bone marrow, the liver, the platelets, and/or platelet precursors. For example, the LLL generator device can be a monochromatic laser and/or a light emitting diode (LED) configured to generate the LLL. The parameter can be at least one of an on time, an off time, a light density, a power, a power density, and an output characteristic. In some instances, the energy of LLL can be delivered in vivo, while in other instances, the energy of LLL can be delivered in vitro. In instances of in vivo operation, the method can include administering LLL noninvasively over an area of a patient's body that includes one or more platelet-making bones. Alternatively, LLL can be applied directly to the platelet-making bone marrow and/or liver by an invasive technique, such as a laser probe catheter. In certain instances, a method of enhancing platelet biogenesis in a patient can include administering thrombopoietic agents in conjunction with LLL to increase the platelet quantity, such as interleukin 11 (IL-11), thrombopoietin (TPO), TPO peptide or non-peptide mimics, and drugs for enhancing or stimulating mitochondrial biogenesis. In some examples, a method of extending platelet storage can include adding platelet additive solution (PSA) configured to enhance platelet function during long-term storage. In some instances, a method of extending platelet storage can include using ultraviolet-A or -C radiation in conjunction with LLL to reduce pathogen contamination during long-term storage.

In another aspect, the present disclosure can include a system that can include a controller device and a LLL generator device (e.g., a monochromatic laser and/or a light emitting diode (LED)). The controller device can include a non-transitory memory and a processor and be configured to generate a control signal comprising a parameter for the LLL application. The LLL generator device can be configured to receive the control signal, generate the LLL based on the parameter, and apply the generated LLL to at least one of bone marrow, liver, and stored platelets or platelet precursors. The parameter can include at least one of an on time, an off time, a light density, a power, a power density, and an output characteristic.

In a further aspect, the present disclosure can include a method that can be performed by a LLL generator device. The method can include receiving a control signal from a controller device that can include a parameter for the LLL application. The method can also include obtaining the parameter from the control signal and applying LLL (wavelength from 600 nm to 1500 nm) to at least one of bone marrow and liver to facilitate the generation of at least one of platelets and platelet precursors (e.g., MKs) according to the parameter. The parameter can include an on time, an off time, a light density, a power, a power density, and/or an output characteristic.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
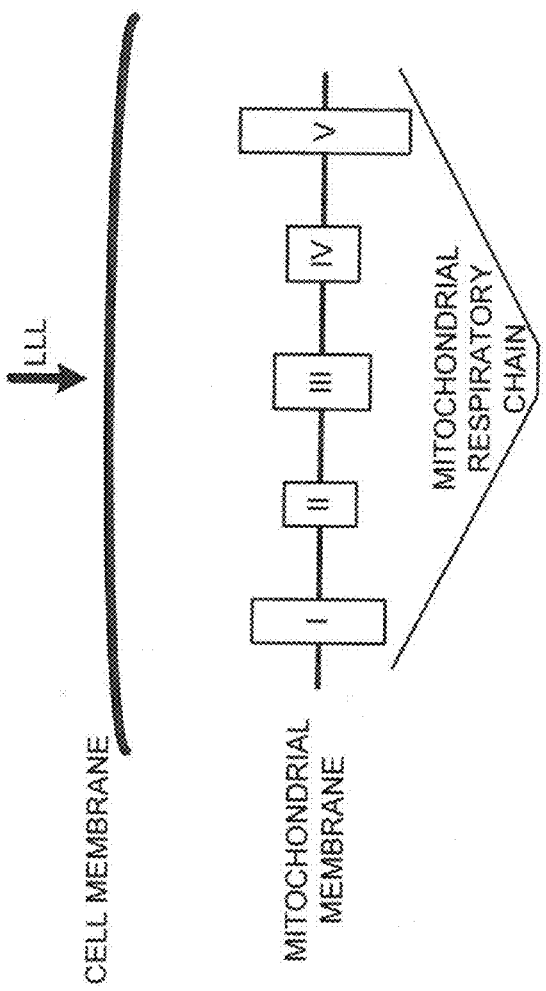
FIG. 1 is a schematic diagram illustrating a mechanism by which low level light (LLL) can act on cells.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "low level light (LLL)" can refer to a procedure that involves exposing cells (e.g., stem cells, other types of platelet precursor cells, platelets, etc.), tissue and/or at least a portion of a patient's body (e.g., platelet-making bone in adults or bone and livers in infants) to low levels of red and near infrared (NIR) light at energy densities that are low compared to other forms of laser therapy (e.g., ablation, cutting, thermal coagulation, etc.). As used herein, the term LLLT ("low level light therapy") can be used interchangeably with LLL).

As used herein, the term "bone marrow" can refer to a tissue inside bone which facilitates the biogeneration of platelets. However, when referring to applying LLL to bone marrow, it will be understood that LLL can be applied to a patient's skin or bone surrounding the actual bone marrow. The same is true for LLL being applied to the patient's liver (e.g., when the patient is a newborn or a neonate, for example).

As used herein, the term "platelet" can refer to a blood cell that contains fragments of cytoplasm and no nucleus that contributes to homeostasis by contributing to the process of stopping bleeding (or clotting). In some instances, platelets can be biogenerated within the bone marrow and/or the liver.

As used herein, the term "platelet precursor" can refer to any cell within the bone marrow and/or the liver that contributes to platelet biogenesis. Example platelet precursors can include hematopoietic stem cell precursor cells, hematopoietic stem cell, megakaryocytes, and the like.

As used herein, the terms "biogenesis" or "biogeneration" can refer to the synthesis of a biological substance. The term "platelet biogenesis" can refer to the synthesis of platelets, platelet precursors, etc.

As used herein, the terms "subject" and "patient" can refer to any warm-blooded living organism including, but not limited to, a human being, a pig, a rat, a mouse, a dog, a cat, a goat, a sheep, a horse, a monkey, an ape, a rabbit, a cow, etc.

Low Level Light

Generally, low level light (LLL) can be applied (in one dose or in multiple doses) to cells (e.g., stem cells, megakaryocytes, other platelet precursor cells, platelets, etc.), tissue (e.g., bone marrow and/or liver), and/or at least a portion of a patient's body at energy densities that are low compared to other forms of laser therapy (e.g., ablation, cutting, thermal coagulation, etc.). For example, the LLL energy density can be from 0.001 J/cm$^2$ to 30 J/cm$^2$. As another example, the LLL energy density can be from 0.001 J/cm$^2$ to 20 J/cm$^2$. In a further example, the LLL energy density can be from 0.1 J/cm$^2$ to 0.5 J/cm$^2$. The present disclosure relates to the application of LLL to enhance both in vivo and in vitro platelet biogenesis and to extend platelet lifespan in both in vivo circulation and in vitro storage. LLL is a simple, non-invasive, safe, convenient, and cost-effective modality that has been clinically employed for decades for pain relief and other applications. The LLL used herein, in some examples, can have a wavelength from 600 nm to 1500 nm. In other examples, the LLL can have a wavelength from 600 nm to 1100 nm. In still other examples, the LLL can have a wavelength from 900 nm to 1000 nm.

While not wishing to be bound by theory, it is believed that LLL can be employed to enhance both in vivo and in vitro platelet biogenesis and to extend platelet lifespan in both in vivo circulation and in vitro storage at least because LLL can enhance ATP synthesis within cells and/or platelets. It is believed that mitochondria are a likely site for the initial effects of LLL. As shown schematically in FIG. 1, the LLL can excite several protein complexes (e.g., I, III, and/or IV,) in the mitochondrial respiratory chain (MRC). Normally, the MRC can produce more than 90% of the ATP in the cell, but the level of ATP synthesis would be reduced in a cell under stress, so with LLL, the amount of ATP within the cell can increase. In some instances, the LLL can lead (additionally or alternatively to the increased of ATP synthesis) to enhanced oxidative phosphorylation, enhanced mitochondrial membrane potential, reduced oxidative stress, and anti-apoptosis.

Platelet Biogenesis

Figure 2:
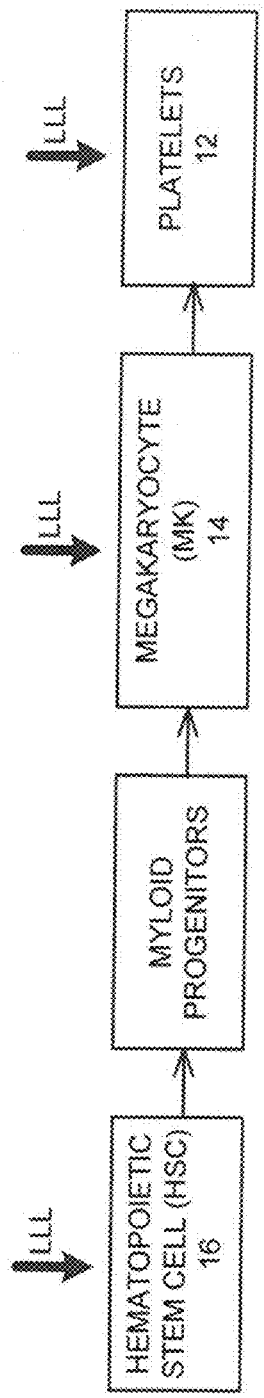
FIG. 2 is a schematic diagram showing a path of platelet generation.

In one aspect, LLL can promote both in vivo and in vitro platelet biogenesis. Additionally, LLL can also prolong the lifespan of the platelets already circulating in the blood. As shown in FIG. 2, platelets 12 can be formed from mature megakaryocytes (MKs) 14 (large bone marrow cells), which can be produced from hematopoietic stem cells (HSCs) 16. Accordingly, platelets can be formed from MKs 14 in a patient's bone marrow and/or liver and then enter the patient's blood for circulation through the patient's body. For example, to facilitate platelet biogenesis, LLL can act on the HSCs 16, the MKs 14, the platelets 12, and/or other progenitors.

In some instances, the LLL can be applied to a portion of the patient's body as a single dose. In other instances, the LLL can be applied to one or more portions of the patient's body in multiple doses. Moreover, in some instances, the LLL application can be non-invasive. In other instances, the LLL application can be invasive. For instance, LLL can be administered transcutaneously and/or subcutaneously, so that it is transmitted into bone marrow, via one or more optical fibers (biodegradable/non-biodegradable, flexible/rigid, etc.) and/or via a mesh formed over an area of marrow-containing bone. Regardless of the source or the output, the LLL energy density at the bone marrow and/or liver can be from 0.001 J/cm$^2$ to 30 J/cm$^2$. Preferably, the LLL energy density at the bone marrow and/or liver can be from 0.001 J/cm$^2$ to 20 J/cm$^2$. More preferably, the LLL energy density at the bone marrow and/or liver can be from 0.1 J/cm$^2$ to 0.5 J/cm$^2$.

In some instances, the LLL can be applied in conjunction with the administration of one or more pharmaceutical treatments. Examples of pharmaceutical treatments that can be administered with the LLL can include, but are not limited to: agents that can promote megakaryopoiesis (e.g., thrombopoietin and its derivatives, any activators or stimulators via thrombopoietin receptor, IL-6, IL-11, etc.), agents or chemical compounds or diet supplements that can enhances mitochondrial biogenesis, mitochondrial activity or improve mitochondrial functions (e.g., CoQ, metabolic substrates like pyruvate, lactate, glucose, vitamin D, etc.), growth factors and their analogs or peptides that can enhance the generation of megakaryocytes or myeloid progenitors, like colony stimulating factor (CSF), GM-CSF, platelet-derived growth factor (PDGF), megakaryocyte growth and development factors (MGDF). Examples of clinically-available agents that can be used in connection with LLL include, but are not limited to: Nplate/Romiplostim (Amgen)-fusion protein analog of thrombopoeitin; Promacta/Eltrombopag (Ligand/GSK) for ITP, a small molecule agonist to the c-mpl (human TPO receptor), the target of thrombopoeitin; Neumega/Oprelvekin (Wyeth/Pfizer)-recombinant interleukin-11, avatrombopag (Eisai, liver disease associated, PhIII), and CpG free thrombopoeitin gene therapy (InvivoGen, pre-clinical).

Figure 3:
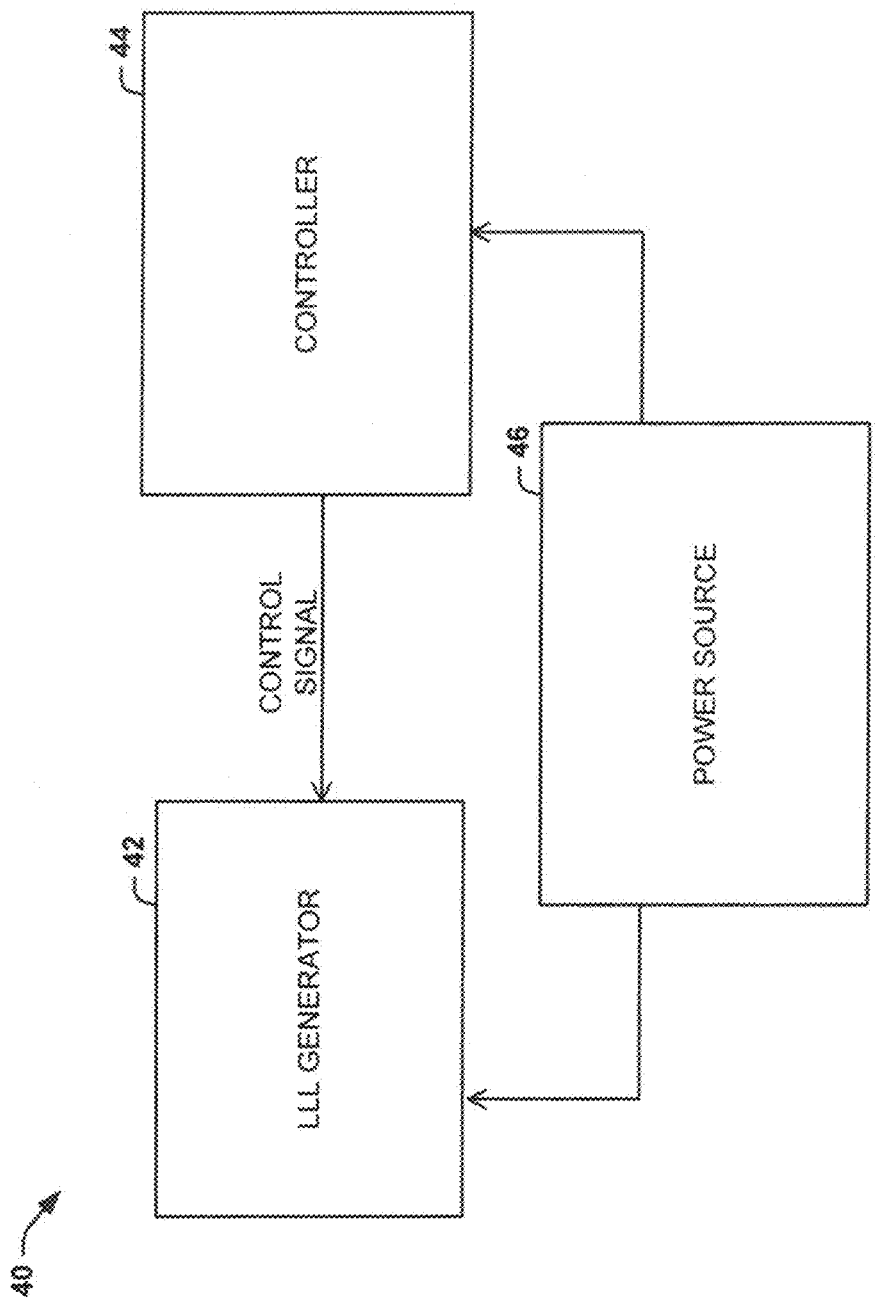
FIG. 3 is a schematic block diagram of a system that can apply LLL to facilitate platelet biogenesis, according to an aspect of the present disclosure.

As shown in FIG. 3, application of the LLL can be controlled by a system 40 that can include a LLL generator 42, a controller 44, and a power source 46. The power source 46 can be configured to supply an operating power to the controller 44 and/or the LLL generator 42. In some instances, the controller 44 and/or the LLL generator 42 can be electrically coupled to the power source 46. For example, the power source 46 can be a device that is configured to generate a power signal (e.g., including enough power to power up the controller 44 and/or the LLL generator), such as a battery power source, a line power source (e.g., a plug), or the like. In other instances, the power source can include at least two power sources (e.g., one to power the LLL generator 42 and one to power the controller 44).

The controller 44 can be configured to generate and transmit a control signal (e.g., including dosage parameters for LLL) to the LLL generator 42. The controller 44 can be a computing device (e.g., a general purpose computer, special purpose computer, and/or other programmable data processing apparatus) that can include or be otherwise associated with a non-transitory memory storing instructions (e.g., computer program instructions) that, upon execution by a processor, can create a mechanism for implementing the functions of the controller 44 (e.g., generating and transmitting the control signal to the LLL generator 42). For example, one or more of the dosage parameters can be pre-set within the controller 44. As another example, one or more of the dosage parameters can be input by a user via a user interface associated with the controller 44.

Figure 4:
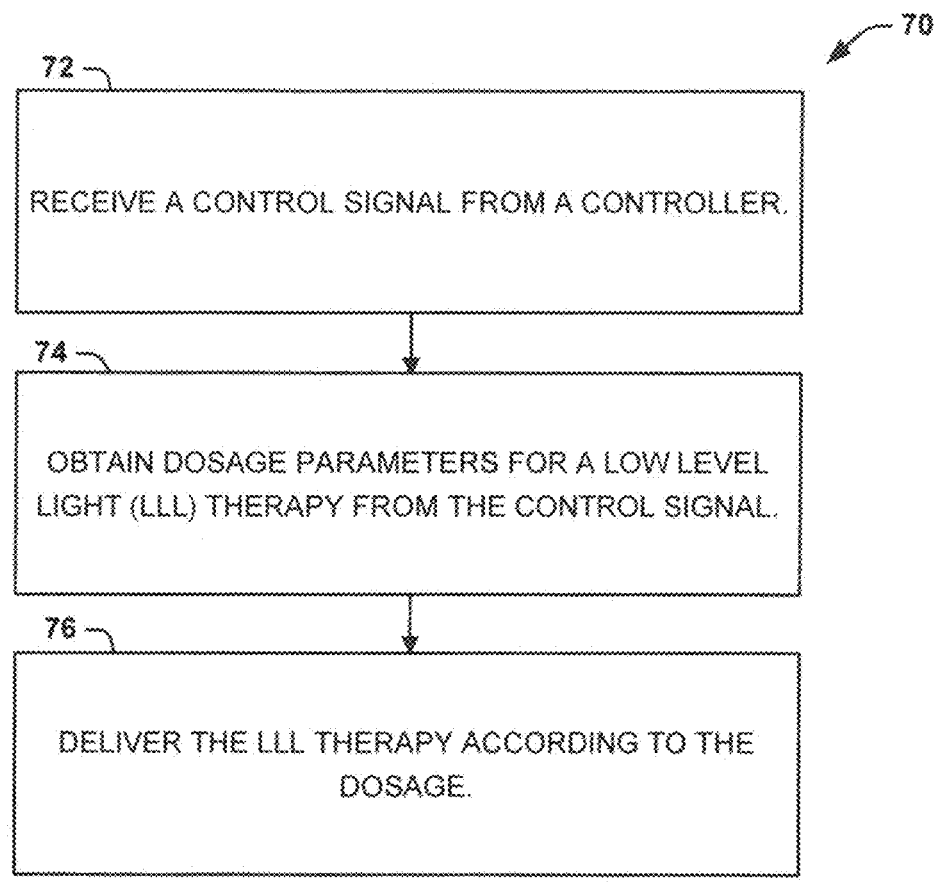
FIG. 4 is a process flow diagram illustrating a method for delivering LLL to facilitate platelet biogenesis that can be employed by the low level light (LLL) generator of FIG. 3.

The controller 44 and the LLL generator 42 can be communicatively coupled (e.g., via a wired connection and/or a wireless connection) to facilitate the transmission of the control signal. An example of a method 70 that the LLL generator 42 can utilize to apply the LLL according to the control signal is shown in FIG. 4. At 72, the LLL generator 42 can receive the control signal from the controller 44. The control signal can include dosage parameters, including an on time, an off time, a light density, a power (e.g., between 1 mW and 1000 mW), a power density e.g., between 0.1 mW/cm$^2$ and 5 W/cm$^2$), and an output characteristic (pulsed (frequency=1 Hz-500 Hz) or continuous).

In some instances, the desired power density can be selected from 0.1 mW/cm$^2$ to 50 mW/cm$^2$ to be directly delivered to platelet-making bones. In some instances, to deliver the desired power density into bone marrow cavities and blood vessels, a relatively higher surface power density of LLL may be required, depending on patient's skin pigmentation, the location of the target bone or vessel, and the depth of the bone or vessel relative to the skin surface. In some embodiments, super pulsed GaAs laser may be employed to generate super pulses of LLL with extremely short duration (100 to 300 nanoseconds), that can penetrate into tissue depths of 3 to 13 cm and deeper.

At 74, the LLL generator 42 can obtain the dosage parameters for the LLL from the control signal. At 76, the LLL generator 42 can deliver the LLL according to the dosage. In some instances, the dosage can include a desired power density (e.g., selected from 0.1 mW/cm$^2$ to 50 mW/cm$^2$) to be delivered to target cells (e.g., MKs inside the bone marrow cavities, circulating platelets in the blood vessels, and stored platelets in storage bags). To deliver the desired power density into bone marrow cavities and blood vessels, a relatively higher surface power density of LLL may be required, depending on patient's skin pigmentation, the location of the target bone or vessel, and the depth of the bone or vessel relative to the skin surface. In some instances, super pulsed GaAs lasers can be employed to generate super pulses of LLL with extremely short duration (100 to 300 nanoseconds), that can penetrate into tissue depths of 3 to 13 cm and deeper to illuminate platelet-making bones.

The LLL generator 42 can be configured to apply LLL to a patient's body (e.g., the whole body or a portion of the body including bone marrow) and/or to an in vitro preparation based on the control signal. In some instances, the LLL generator 42 can include a monochromatic laser that radiates light in the red or NIR wavelengths ($\lambda$=600 nm-1500 nm). In other instances, the LLL generator 42 can include a light emitting diode (LED) that radiates light in the red or NIR wavelengths ($\lambda$=600 nm-1500 nm).

In some instances, the LLL generator 42 can be configured to apply the LLL to the patient's body according to the control signal. In some instances, the LLL can be applied to a portion of the patient's body (e.g., vertebrae, pelvis, ribs, sternum, femur, tibia, etc.). One example of the LLL generator 42 that can deliver the LLL to the portion of the patient's body is a LLL blanket. The LLL blanket can be wrapped around a portion of the patient's body to deliver the LLL according to the control signal. Another example of the LLL generator 42 is a LLL vest. The LLL vest can cover the patient's vertebrae, sternum, and ribs to deliver LLL according to the control signal. Yet another example of the LLL generator 42 is an LLL chair. A patient can sit on the LLL chair, which can deliver the LLL to the patient's vertebrae, pelvis, ribs and/or sternum according to the control signal. In another example, an LLL bed can be arranged similarly to a tanning bed to deliver LLL to at least a portion of the patient's body. In each example, the LLL can provide a safe and effective mechanism that can promote platelet regeneration and extend the life of circulating platelets in vivo. Accordingly, in one example, LLL can provide a primary or secondary prophylaxis that can increase the number of platelets in the blood of a patient with thrombocytopenia, potentially reducing the need for platelet transfusions.

In another example, the LLL generator 42 can be configured to apply the LLL to an in vitro preparation according to the control signal to facilitate the generation of platelets. Due to the increasing demand of platelet transfusions each year, platelet shortages are common due to both limited donors and the short (5-day) shelf life for the stored platelets. To alleviate these shortages, much effort has been put into the development of donor-independent platelet generation in vitro using newly developed stem cell technologies. However, these stem cell technologies often lead to growing-limited processes for in vitro platelet generation. For example, in vitro platelet generation from CD34$^+$ stem cells is a relatively low rate of platelet production. However, LLL can significantly increase the rate of platelet production in vitro, either alone or in combination with other agents, enhancing the yield of platelet biogenesis from MKs or various stem cell technologies. In some instances, additional factors that facilitate platelet growth or mitochondrial activity, also can be added to the in vitro preparation to further promote the biogenesis of platelets in vitro.

Platelets can be generated in vivo from various stem cells, including both natural occurring and synthesized stem cells. LLL can be applied alone and/or in combination with one or more agents to induce platelet biogenesis in vitro. In some instances, LLL can promote platelet production from umbilical cord stem cells (ESC), induced pluripotent stem cells (iPSC), or other types of induced stem cells that can differentiate into myeloid progenitors and/or platelets.

It has been shown experimentally that LLL can promote platelet biogenesis. The following experimental results are shown for the purpose of illustration only and are not intended to limit the scope of the appended claims.

Figure 5:
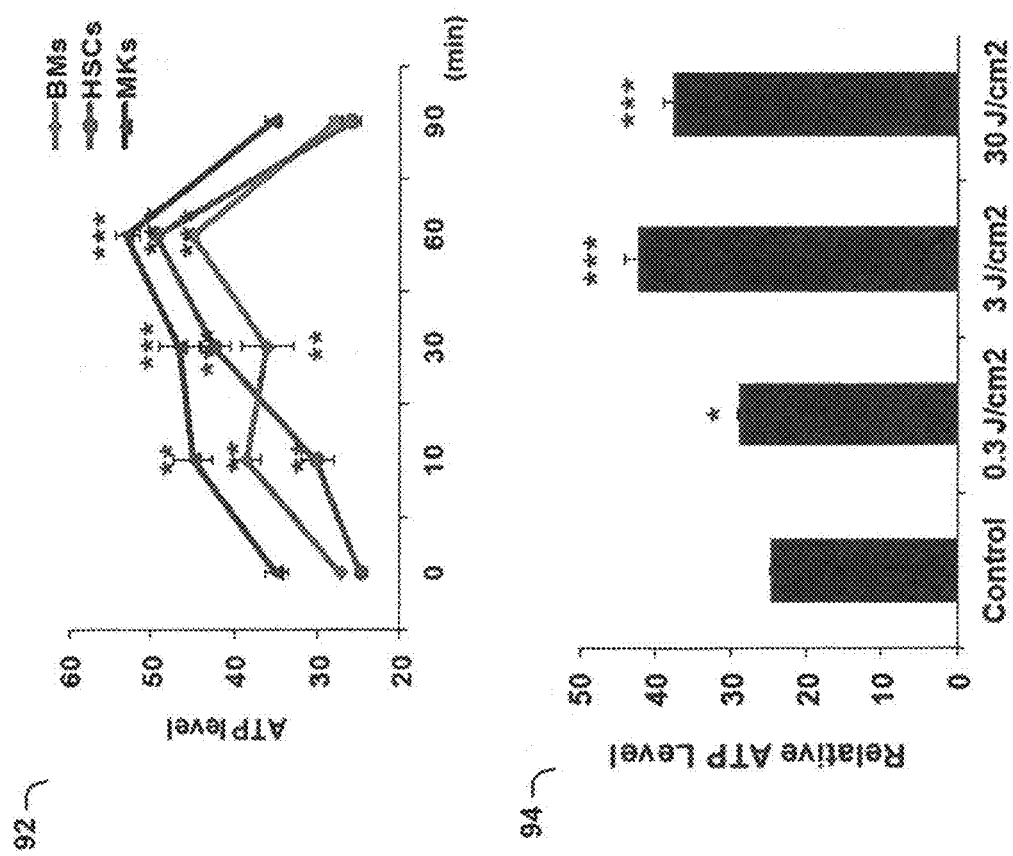
FIG. 5 is an experimental result showing that LLL increases the ATP synthesis in murine thrombopoietic cells.

As shown in FIG. 5, LLL increases the ATP synthesis in murine thrombopoietic cells. The graph 92 illustrates how LLL enhances ATP synthesis in these thrombopoietic cells. Megakaryocytes (MKs), hematopoietic stem cells (HSCs), and bone marrow (BM) cells were prepared from 8-week-old C57BL/6 mice, and exposed to 810-nm diode laser at a power density of 10 mW/cm$^2$ for 5 min at an energy density (also called fluence) of 3 J/cm$^2$. The LLL treatment increased ATP formation immediately in these cells, which peaked at 60 min before returning to a base level in 90 min after LLL. The chart 94 illustrates the effects of various fluences from 0.3 to 30 J/cm² on ATP synthesis at 30 min post-LLL in MKs. n=6, *P<0.05, ***P<0.001 compared to non-LLL-treated controls.

Figure 6:
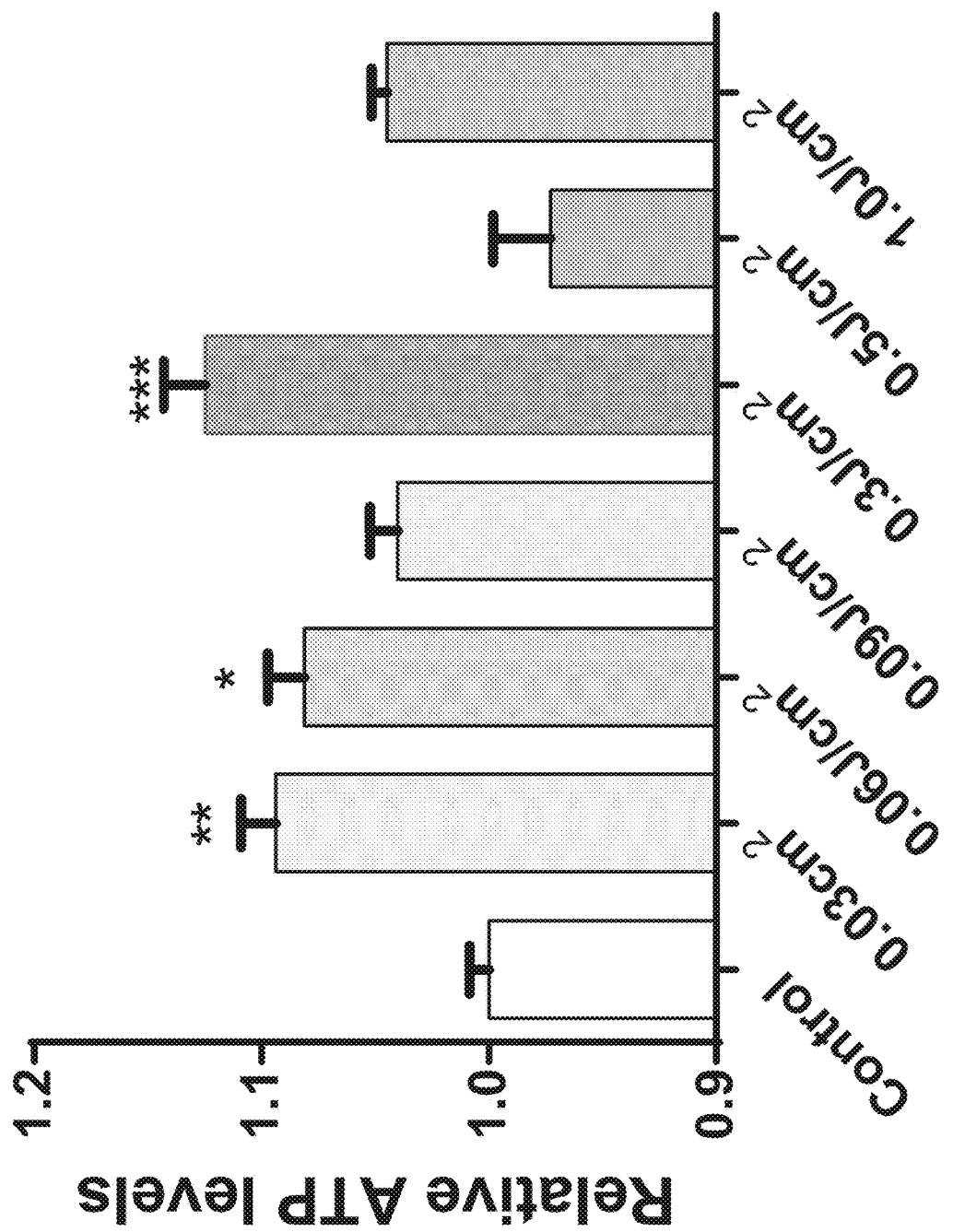
FIG. 6 is an experimental result showing that LLL at a wavelength of 980 nm augments ATP production in MKs ex vivo at much lower energy levels.

LLL at longer wavelengths (e.g., from a 980 nm laser) at lower energy densities (mJ/cm²) can augment ATP production in bone marrow cells of B6 mice. Platelets are formed from MKs in red bone marrow and released into the circulation. Hematopoietic stem cells (LSKs) were sorted from bone marrow cells of B6 mice and differentiated into MKs for 5 days in serum-free expansion medium supplemented with 100 ng/ml thrombopoietin (TPO), named MK medium. The MKs were illuminated with 980 nm laser light with continuous wavelength (CW) at indicated energy densities (FIG. 6). ATP in these MK cultures was measured 1 hr post-LLLT. The laser light at a wavelength of 980 nm was found to enhance ATP production in the cells at an energy density as low as 0.03 J/cm², which is 100-fold lower than that of 810 nm laser that stimulated ATP production in MKs at 3 J/cm² under similar conditions. Notably, at a higher energy density ≥3.5 J/cm², 980 nm laser did not enhance ATP production significantly.

Figure 7:
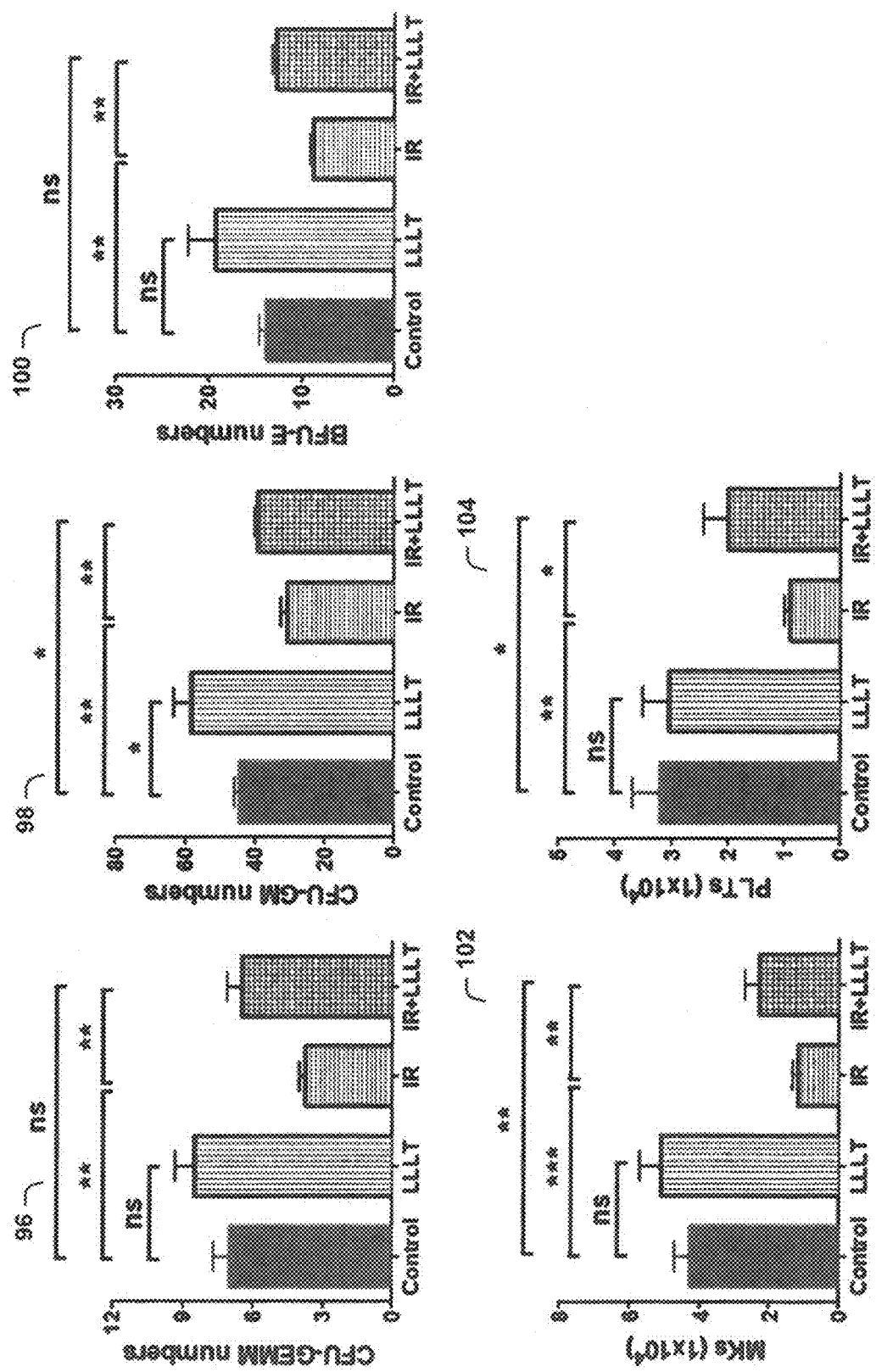
FIG. 7 is an experimental result showing that LLL enhances HSC differentiation ex vivo, in particular, after stress.

As shown in FIG. 7, LLL enhances HSC differentiation ex vivo. Murine HSCs were prepared from 8-week-old C57BL/6 mice and treated with or without 3-Gy γ-irradiation (IR), followed by a single dose of 3 J/cm² LLL at 6 hr after γ-irradiation. The treated HSCs were cultured in methylcellulose-based media supplemented with optimal cytokines at 1×10³ cells per 35 mm dish for 14 days. These HSCs produced heterogeneous populations of actively dividing hematopoietic progenitors, forming discrete colonies that can be enumerated and characterized as colony-forming units (CFUs). Compared with non-IR-treatment controls, IR severely reduced the number of Granulocyte-Erythrocyte-Monocyte-Megakaryocyte (CFU-GEMM, chart 96) and Granulocyte-Macrophage (CFU-GM, chart 96), as well as Burst-Forming Units of Erythroid (BFU-E, chart 100), in agreement with myeloid suppression by γ-irradiation. Strikingly, the colony-forming ability of radiated HSCs was significantly restored by LLL (charts 96, 98, 100), with little effect on the differentiation of non-IR-HSC controls. Moreover, when radiated HSCs were cultured in StemSpan expansion medium supplied with a cytokine cocktail that favored HSC differentiation into MKs and platelets, the number of MKs and platelets increased significantly in the presence as compared to the absence of LLL (charts 102, 104), although it did not fully restore thrombopoiesis of these cells. n=4, *P<0.05, P<0.01, *P<0.001 compared to indicated groups. ns, not significant.

Figure 8:
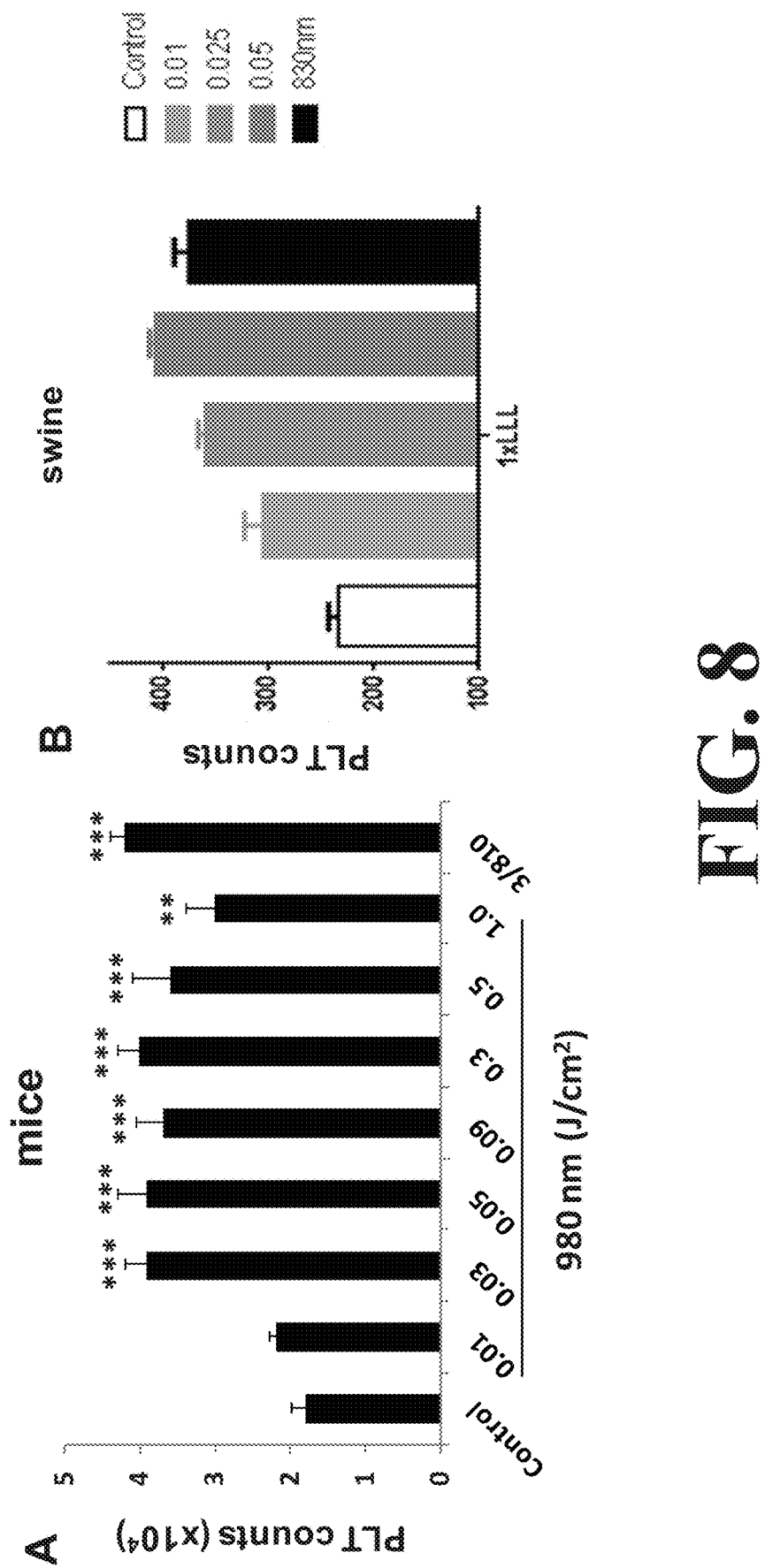
FIG. 8 is an experimental result showing that LLL with a wavelength of 980 nm and lower energy densities enhanced platelet production ex vivo in bone marrow cells isolated from mice and pigs.

Platelet biogenesis can be enhanced ex vivo by LLL at longer wavelengths (e.g., from a 980 nm laser) at lower energy densities (mJ/cm²). The 980 nm laser also enhanced platelet formation from MKs, yet at a much lower laser energy. As shown in FIG. 8, bone marrow cells were isolated from mice or swine (pigs) and differentiated in MK medium for 3 days, after which the cells were illuminated with 980 nm at varying energy densities. Platelets in the culture were measured 3 days later by flow cytometry based on forward/side scatter and CD41 expression. Exposure of MKs to 980 laser at laser energy ranging from 0.025 to 0.05 J/cm² in pigs or 0.03 to 0.5 in mice increased platelet production similarly as 830 nm laser at 3 J/cm².

Figure 9:
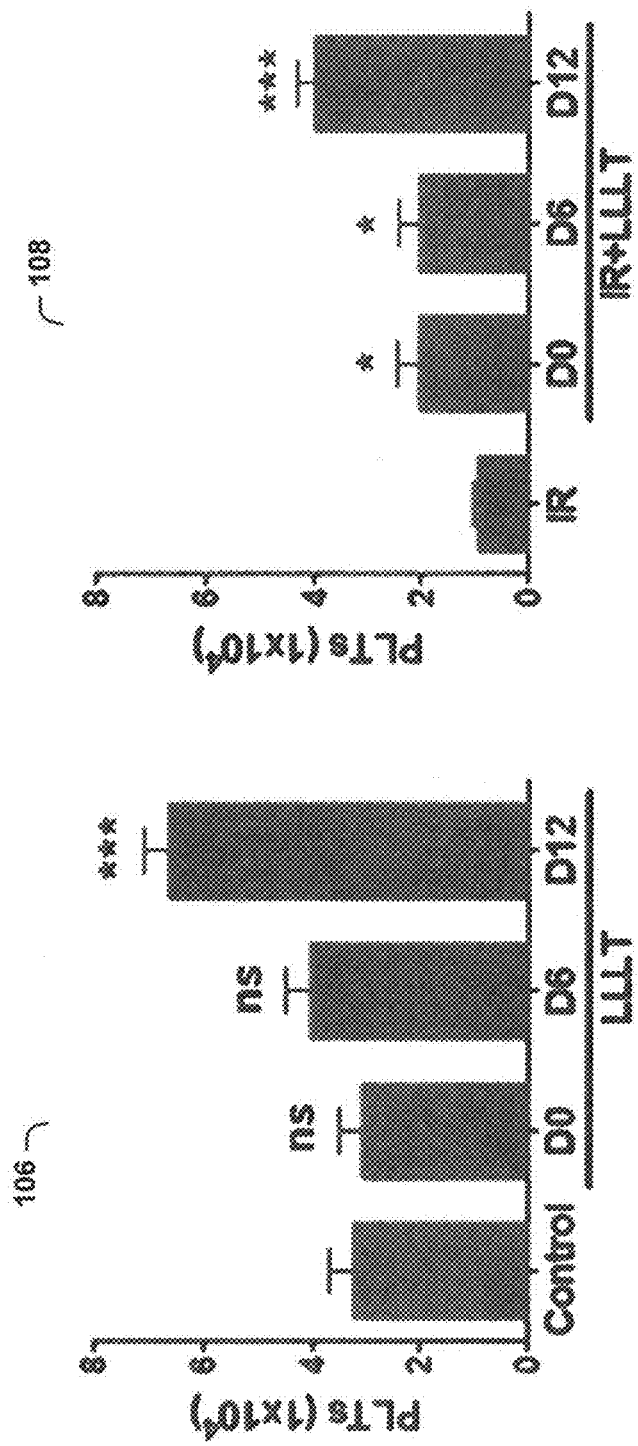
FIG. 9 is an experimental result showing that LLL preferably promotes the differentiation of MKs to platelets.

As shown in FIG. 9, LLL preferably promotes the differentiation of MKs to platelets. To further investigate the thrombopoietic effect of LLL, a single dose of 3 J/cm² LLL was given to non-γ-irradiated (as shown in chart 106) and 3-Gy γ-irradiated (as shown in chart 108) HSCs at 6 hr (D0), 6 days (D6), or 12 days (D12), respectively, after initial culture. In non-γ-irradiated HSC cultures, LLL administered in 6 hr or day 6 after γ-irradiation showed no significant influence over control groups. Platelet counts were increased robustly only when LLL was administered in 12 days of culture (chart 106) and this was a time when a number of MKs reached the highest level in the culture of HSC differentiation. The observation suggests that direct illumination of MKs vigorously promotes platelet generation. Consistent with this, a highest level of platelet production was also seen when γ-irradiated HSC cultures were exposed to LLL on day 12 of the culture as compared to LLL exposure at any other time points. n=6, *P<0.05, P<0.01, *P<0.001, compared to non-treated control groups. ns, not significant.

Figure 10:
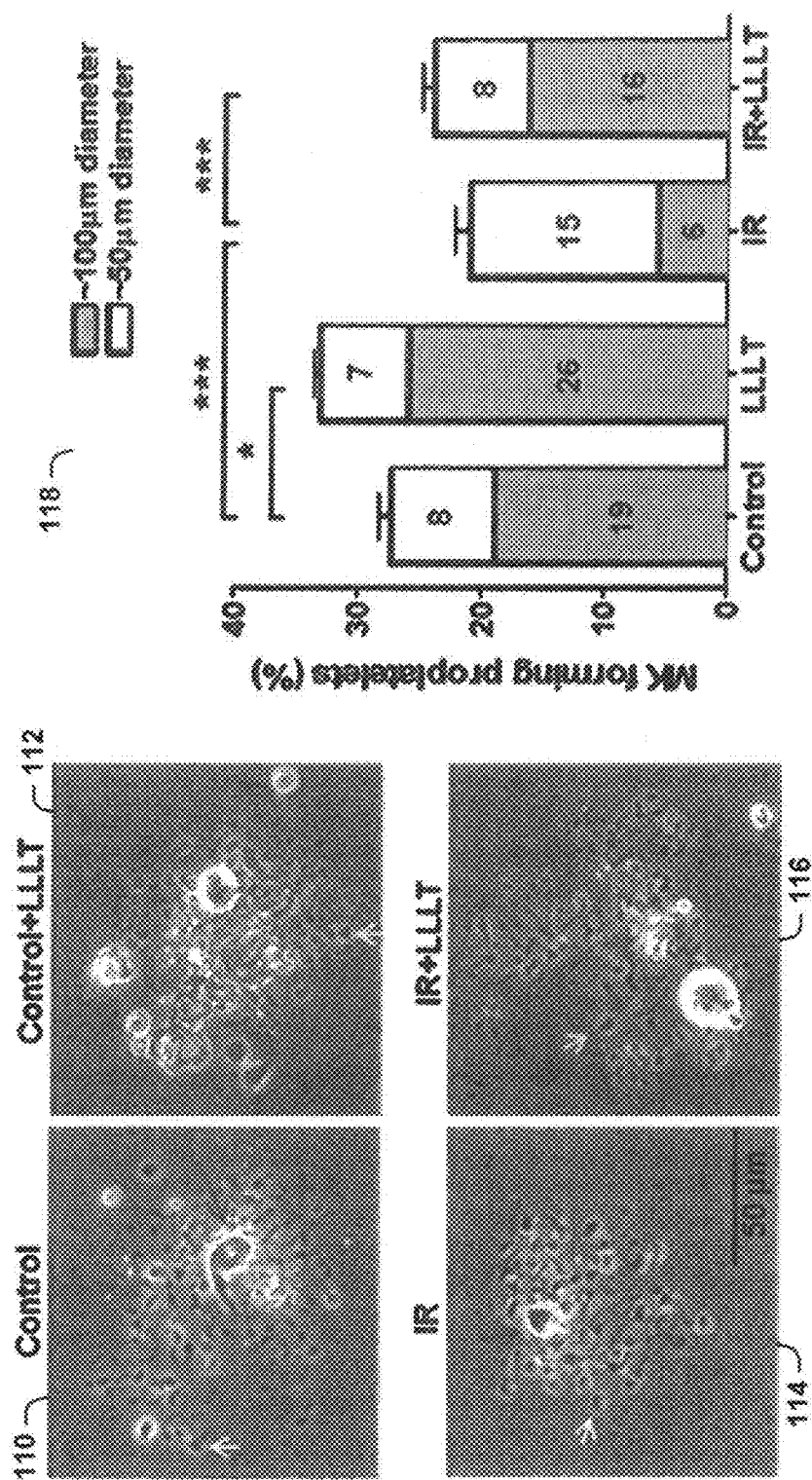
FIG. 10 is an experimental result showing that LLL enhances protoplatelet formation (PPF) ex vivo.

As shown in FIG. 10, LLL enhances proplatelet formation (PPF). Production of platelets from MKs involves an elaborate process that converts the cytoplasm into branched intermediate structures called "proplatelets". Proplatelets are decorated with multiple swellings of a similar size to a platelet, on which the individual platelet develops (pictures 110, 112, 114, and 116). The complex of these branches and the length and number of swellings on each proplatelet determine the quantity of platelets produced from a single MK. To verify that direct illumination of MKs gave rise to the higher level of platelet production, murine MKs were sorted from control mice or γ-irradiated mice in 6 hr after 3-Gy γ-irradiation. The MKs that were exposed to a single dose of 3 J/cm² LLL were differentiated into platelets in medium supplied with 100 ng/ml thrombopoietin (TPO) for 24 hr. Control MKs formed branched proplatelets with abundant swellings on them, and the terminally mature MKs were ~100-μm in diameter on average (picture 110). In contrast, 3-Gy γ-irradiation gave rise to much shorter branches with a fewer swellings on the proplatelets, and the terminally mature MKs were only a half of the normal size (picture 114). Remarkably, a single dose of 3 J/cm² LLL completely normalized proplatelet elongation and swelling, leading to a normal morphology (picture 116). In accordance to this, about 27% of control MKs formed PPF within 24 hrs, and 19% of these cells were mature MKs of 100-μm in diameter. However, only 21% radiated MKs could form PPF, among which only ~6% were normal in size. A single dose of LLL in γ-irradiated MKs increased percentages of large, mature MKs from 6% to 16% (chart 118). LLL also significantly elevated a proportion of non-γ-irradiated MKs with ~100-μm in size (picture 112 and chart 118). n=6, *P<0.05, ***P<0.001 compared to indicated group.

Figure 11:
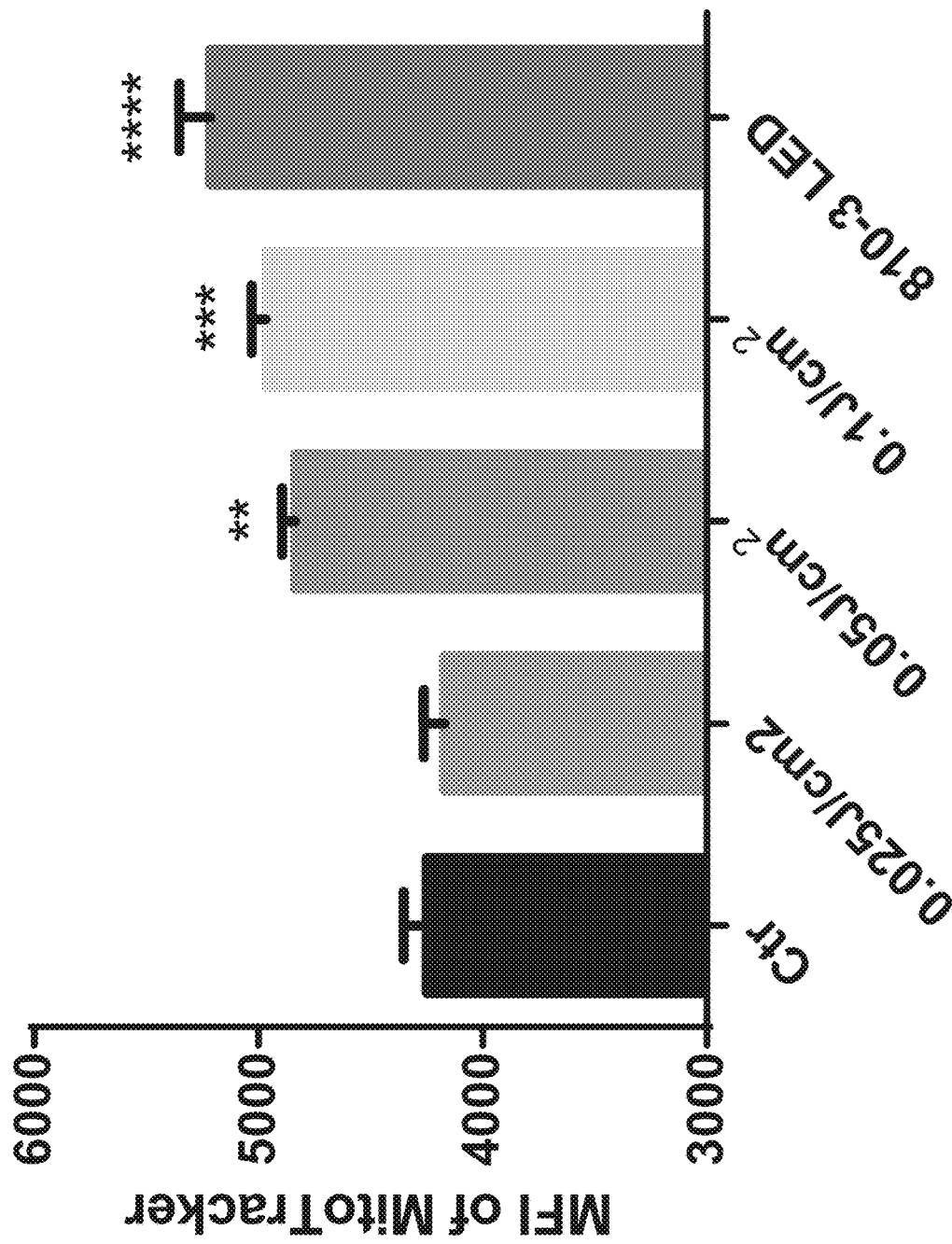
FIG. 11 is an experimental result showing that mitochondrial biogenesis is induced in MKs after exposure to LLL with wavelengths of 980 nm or 810 nm.

LLL at longer wavelengths (e.g., from a 980 nm laser) at lower energy densities (mJ/cm²) can increase mitochondrial biogenesis in MKs, resulting in enlargement of proplatelet-forming MKs and a high rate of platelet production for individual MKs. Similar to 810-830 nm laser, laser at 980 nm also bolstered mitochondrial biogenesis in MKs as evidenced by increasing mitochondrial content in MKs 24 hr after exposure of MKs to varying densities of 980 nm laser as FIG. 11. In the study, MKs were differentiated from embryonic livers dissected from day 13.5 pregnant mice. Mitochondrial contents were increased by 980 nm at 0.05 or 0.1 J/cm² albeit slightly lesser sufficiently than 810 nm laser at 3 J/cm².

Figure 12:
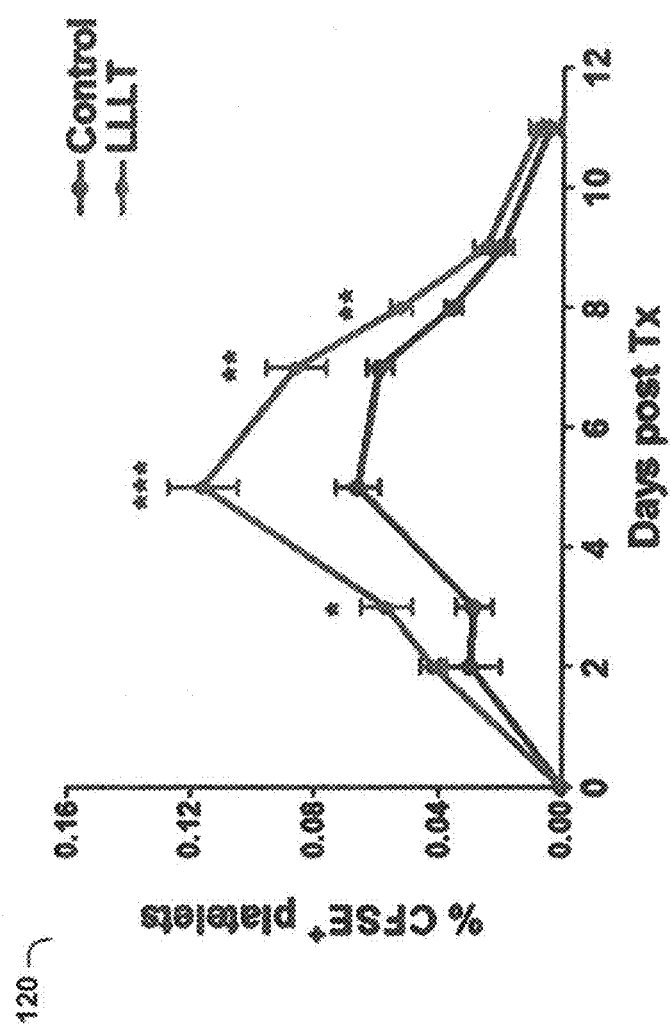
FIG. 12 is an experimental result showing that LLL enhances platelet formation from LLL-treated MKs in vivo.

As shown in FIG. 12, LLL enhances in vivo platelet production by treatment of mature MKs. To confirm more efficient differentiation of MKs to platelets following LLL illumination, CD41⁺ MKs were sorted from donor mice, treated with a single dose of 3 J/cm² LLL, and then labeled with a vital fluorescent dye, carboxyfluorescein succinimidyl ester (CFSE). The labeled MKs were intravenously infused into recipient mice at $1 \times 10^5$ MKs per mouse. The infused MKs produced a higher level of platelets in recipients with LLL than without it. As shown in graph 120, the peak of platelet production from LLL-treated MKs was almost as twice as that of control counterparts. n=8, *P<0.05, P<0.01, *P<0.001.

Figure 13:
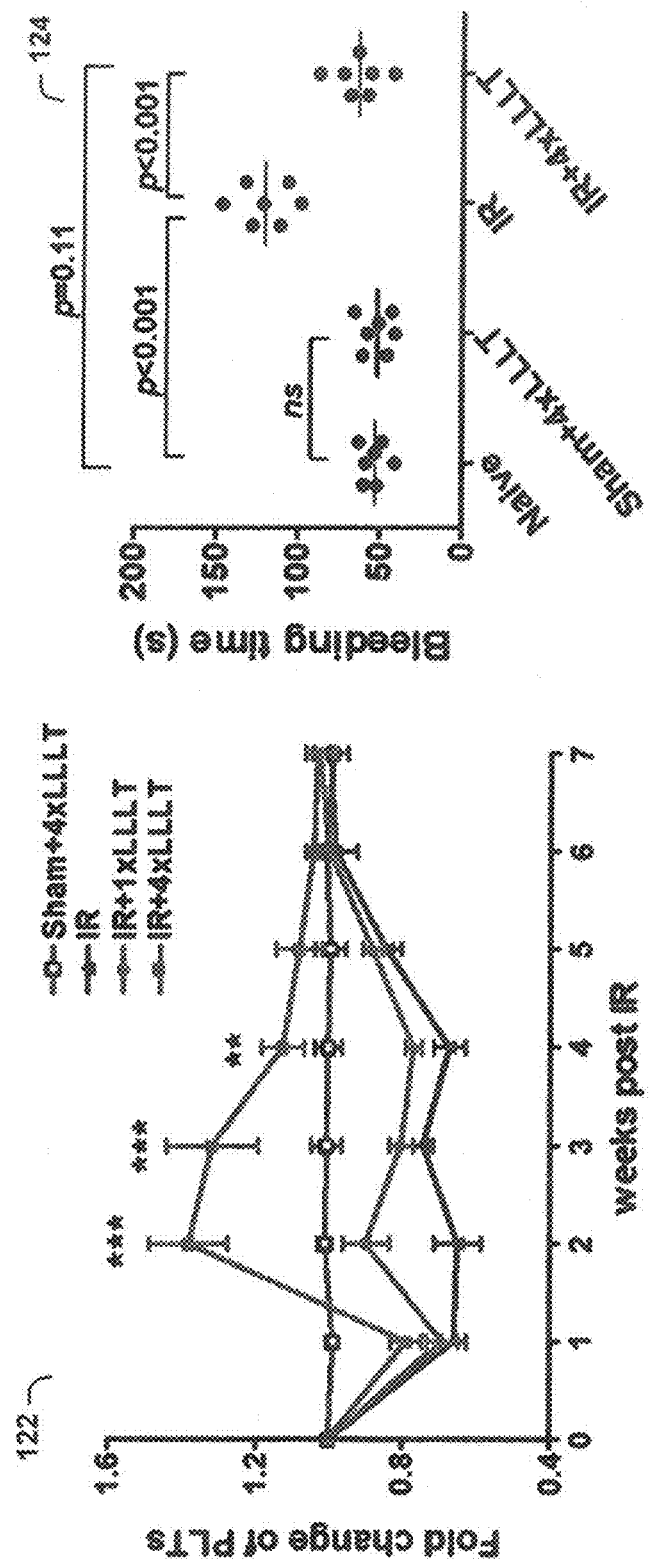
FIG. 13 is an experimental result showing that LLL improves platelet regeneration in mice after γ-irradiation and normalizes bleeding times.

As shown in FIG. 13, LLL improves platelet regeneration in mice after γ-irradiation. C57BL/6 mice at 8-week-old were subjected to 3-Gy whole body γ-irradiation, followed by a whole body exposure to LLL at 6 hr post-γ-irradiation. Two LLL regimens were one exposure with a 808-nm light-emitting diode (LED) at a fluence of 10 $J/cm^2$ (IR+1× LLL); and a total of 4 exposures performed once per day up to 4 days with 10 $J/cm^2$ at each point (IR+4×LLL). Control groups included mice receiving 3-Gy γ-irradiation alone (IR) or 4×LLL alone (Sham+4×LLL). Completed blood counts were checked weekly and compared with IR control mice. LLL increased platelet counts to a pre-γ-irradiation level or above as early as 2 weeks (graph 122, IR+4×LLL) after γ-irradiation, in contrast to a 6-week recovery period in radiated mice without LLL or with only one LLL illumination (n=6, P<0.01, *P<0.001) compared to IR group. In accordance to this, radiated mice that received 4×LLL reduced a tail bleeding time to a normal level, significantly shorter than that in the absence of LLL (P<0.001) when examined 3 weeks post-γ-irradiation (graph 124). Notably, control mice treated with 4×LLL showed little effect on their platelet counts, underscoring a safety of the approach since there would be few concerns about thrombosis even after repeated LLL uses.

Figure 14:
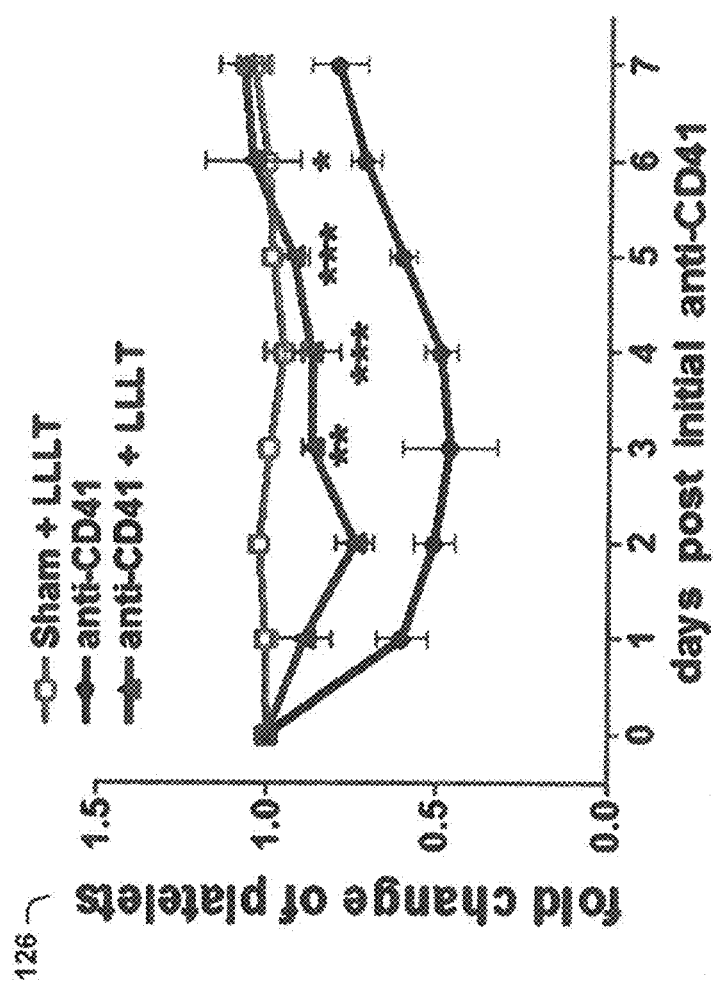
FIG. 14 is an experimental result showing that LLL enhances platelet biogenesis in vivo in the presence of anti-CD41 antibody.

As shown in FIG. 14, LLL enhances platelet biogenesis in vivo in the presence of anti-CD41 antibody. Immune thrombocytopenia (ITP) occurs frequently after repeated platelet transfusions, cancer patients receiving chemotherapy, and patients with autoimmunity against platelets. To mimic immune thrombocytopenia, mice were given anti-CD41 antibody every other day for a week at a dose of 68 μg/kg body weight. Anti-CD41 antibody can bind to platelets, megakaryocytes, and their precursors and triggers platelet depletion in 24 hr after injection. The mice receiving anti-CD41 antibody were illuminated with 36 $J/cm^2$ LED at 830 nm daily for 4 days with an initial illumination at 4 hr after first anti-CD41 injection. The LLL-illuminated mice displayed a much less severe decline in platelet counts in the first 2 days as compared to non-LLL-treated controls. This was followed by accelerating platelet recovery starting at as early as day 3 after anti-CD41 antibody injection. As shown in graph 122, again, there was no effect of LLL on platelet counts in control mice. n=6, *P<0.05, P<0.01, *P<0.001 compared to mice receiving anti-CD41 antibody only.

Figure 15:
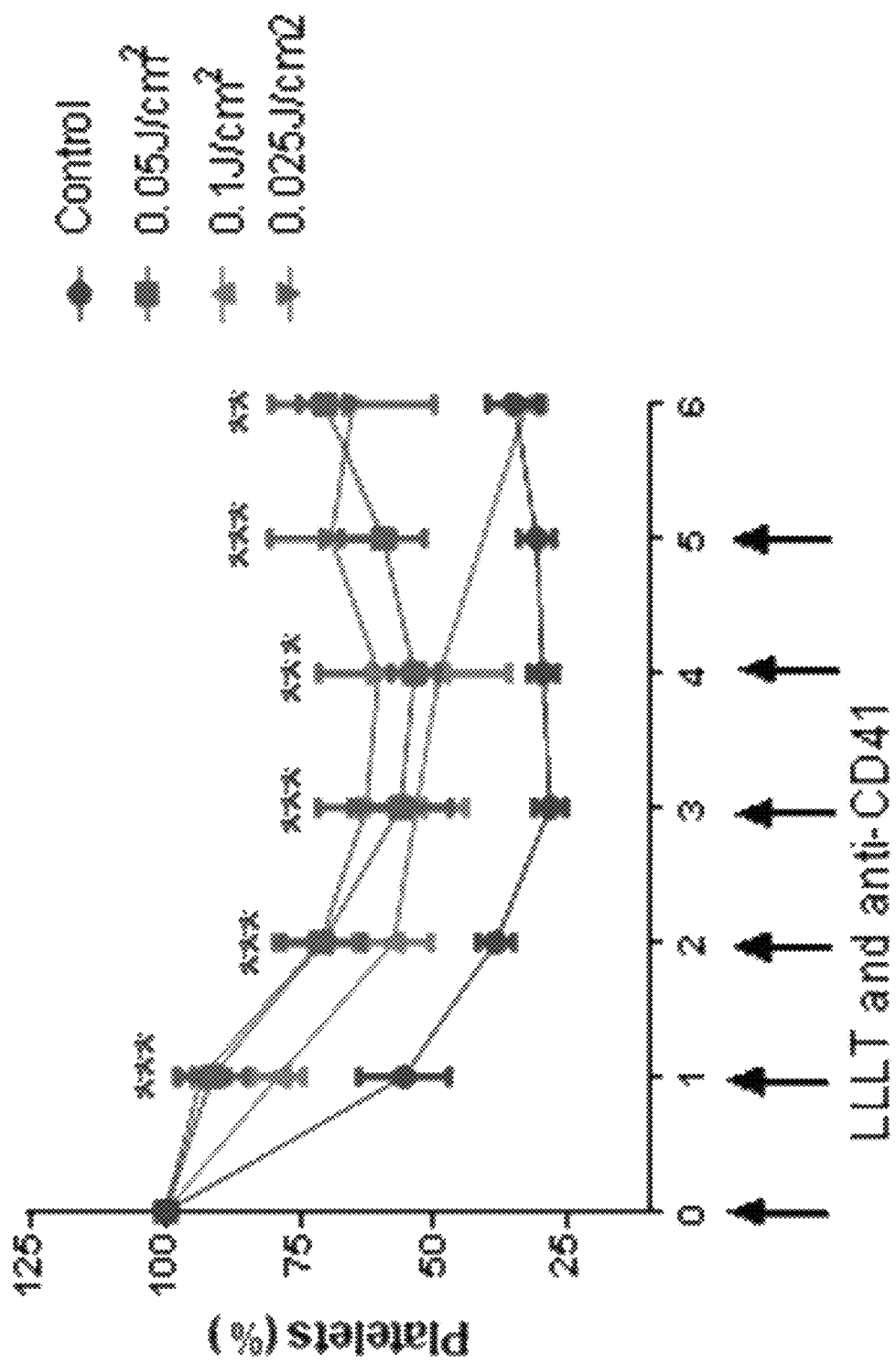
FIG. 15 is an experimental result showing that LLL at a wavelength of 980 nm sustains platelet counts above 50% of the normal platelet counts in the presence of anti-CD41 antibody.

As shown in FIG. 15, the LLL at longer wavelengths (e.g., from a 980 nm laser) at lower energy densities ($mJ/cm^2$) can prevent platelet count drops in mice treated with anti-CD41 antibody. B6 mice at 8 weeks of age were administered anti-CD41 antibody at 0.1 mg/kg/day for 5 consecutive days to deplete platelets, a commonly used immune-induced thrombocytopenia (ITP) model. The ITP mice were exposed noninvasively to 980 nm CW laser at indicated laser doses 4-6 hrs after each antibody injection. The 980 nm laser at 0.025 and 0.05 $J/cm^2$, and to a lesser degree, 0.1 $J/cm^2$ (the laser energy measured within bone marrow) prevented the nadir of platelet counts and sustained platelet counts above 50% of the normal platelet counts in the presence of anti-CD41 antibody.

Platelet Storage

In another aspect, LLL can be used to increase the shelf life of the stored platelets (e.g., applied before storage in an incubator and/or while stored in the incubator). Platelets require special storage conditions, and their storage time is limited due to storage-related mitochondrial injury (e.g., the U.S. Food and Drug Administration has set an expiration date of 5 days for stored platelets). While not wishing to be bound by theory, it is believed that because LLL can sustain mitochondrial functionality under a variety of stresses, LLL can preserve the quality of stored platelets over an extended period of time. For example, LLL can extend a shelf life of stored platelets beyond the FDA-mandated expiration date of 5 days (e.g., to 8 days or more). Increasing the shelf life of platelets can increase the availability of platelets and help to meet an increasing demand of platelet transfusion. Additionally, in some instances, LLL can increase the efficacy of platelet transfusions even with a reduced number of platelets in each transfusion.

Figure 16:
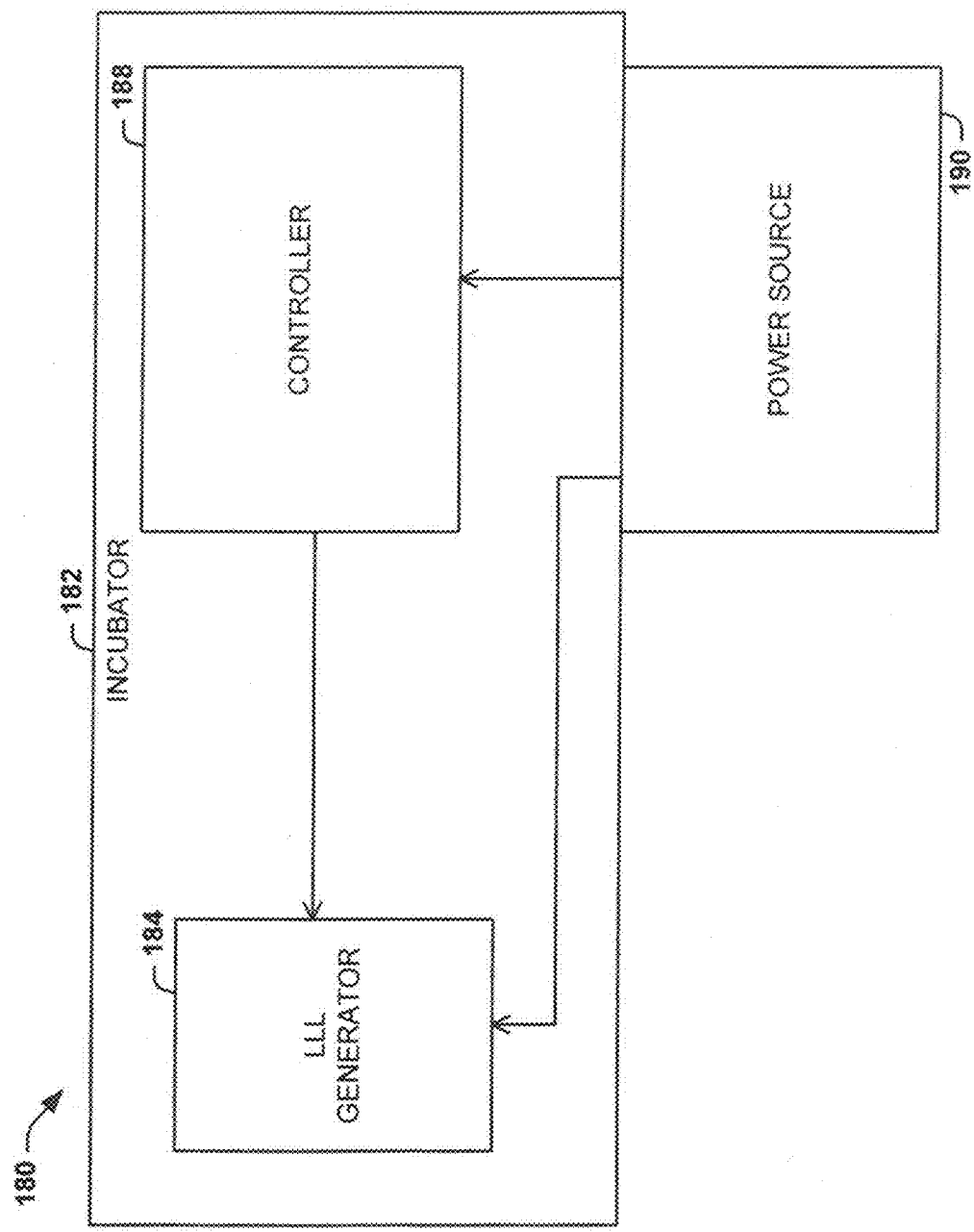
FIG. 16 is a schematic block diagram of a system that can apply LLL to enhance platelet storage, according to another aspect of the present disclosure.

As shown in FIG. 16, application of LLL can be controlled by a system 180 that can be included in incubator 182 with a LLL generator 184, a controller 188, and a power source 190. Although the LLL generator 184 is illustrated as being housed within the incubator 182, in some instances, the LLL generator 184 can be independent from the incubator 182. In both instances, the LLL generator 184 can be configured to deliver the LLL to the stored platelets. LLL with the same conditions described above can be used for platelet storage applications, except where noted.

The power source 190 can be configured to supply an operating power to the controller 188, the incubator 182, and/or the LLL generator 184. In some instances, the controller 188, the incubator 182, and/or the LLL generator 184 can be electrically coupled to the power source 190. For example, the power source 190 can be a device that is configured to generate a power signal (e.g., including enough power to power up the controller 188, the incubator 182, and/or the LLL generator 184), such as a battery power source, a line power source (e.g., a plug), or the like.

The controller 188 can be configured to generate and transmit a control signal (e.g., including parameters for LLL and/or incubation parameters) to the LLL generator 184 and/or the incubator 182. For example, upon execution by the processor, the instructions can create a mechanism for implementing the functions of the controller 188 (e.g., generating and transmitting the control signal to the LLL generator 184 and/or the incubator 182). For example, one or more of the parameters can be pre-set within the controller 188. As another example, one or more of the dosage parameters can be input by a user via a user interface associated with the controller 188. In some instances, the controller 188 can be a computing device (e.g., a general purpose computer, special purpose computer, and/or other programmable data processing apparatus) that can include a non-transitory memory that stores instructions (e.g., computer program instructions) and a processor that can be configured to execute the instructions.

Figure 17:
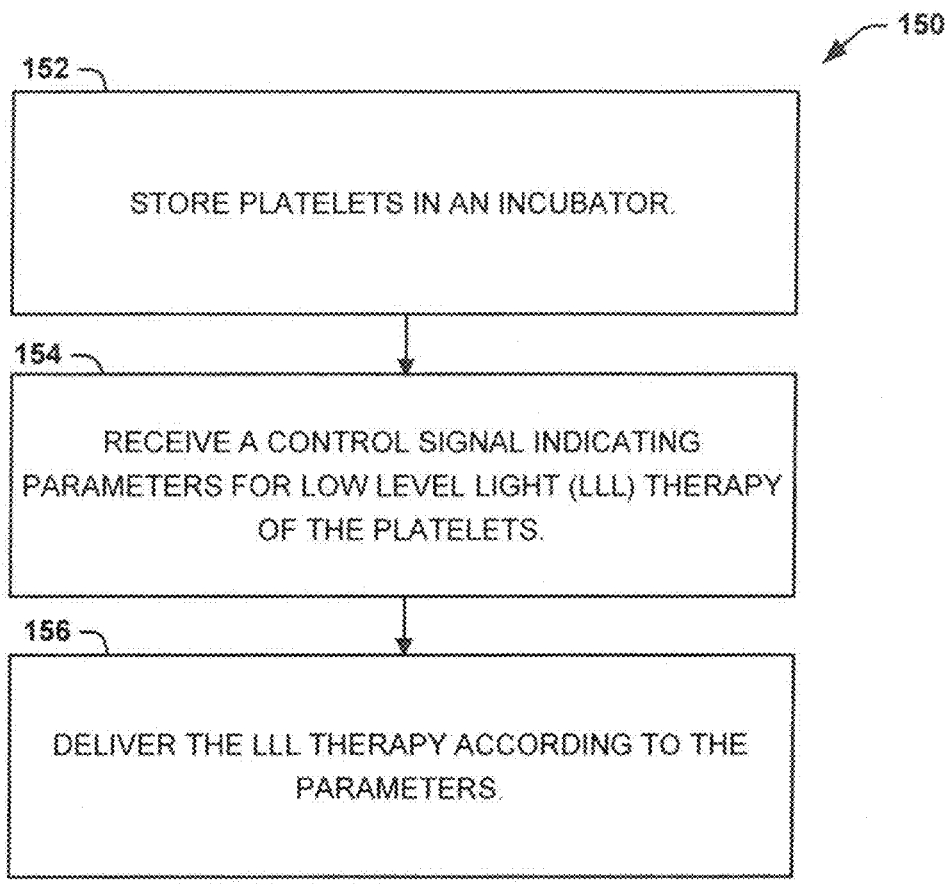
FIG. 17 is a process flow diagram illustrating a method for delivering LLL to enhance platelet storage that can be employed by the LLL generating incubator of FIG. 14.

The controller 188, the incubator 182, and/or the LLL generator 184 can be communicatively coupled (e.g., via a wired connection and/or a wireless connection) to facilitate the transmission of the control signal. An example of a method 150 that the LLL generator 184 can utilize to apply the LLL according to the control signal is shown in FIG. 17. At 152, the platelets can be stored in the incubator 182. At 154, the LLL generator 184 can receive the control signal from the controller 186. The control signal can include parameters for the LLL, including an on time, an off time, a light density, a power (e.g., between 1 mW and 1000 mW), a power density e.g., between 0.1 mW/cm² and 5 W/cm²), and an output characteristic (pulsed (frequency=1 Hz-500 Hz) or continuous). At 156, the LLL generator 184 can deliver the LLL to the platelets according to the parameters.

The LLL generator 184 can be configured to apply LLL to stored platelets based on the control signal. In some instances, the LLL generator 184 can include a monochromatic laser that radiates light in the red or NIR wavelengths (λ=600 nm–1100 nm). In other instances, the LLL generator 184 can include a light emitting diode (LED) that radiates light in the red or NIR wavelengths (λ=600 nm-1100 nm).

In some instances, the LLL generator 184 can be integrated into the current platelet storages mechanisms. For example, the LLL generator 184 (e.g., a LED array) can be integrated into a flatbed to deliver the LLL to stored platelets. In some instances, the flatbed can be integrated within an incubator 182 to apply the LLL to the stored platelets throughout their storage period.

It has been shown experimentally that LLL can enhance platelet storage. In brief, the following data clearly suggest that LLL can sustain mitochondrial function during platelet storage, leading to far smaller reductions in ATP production, pH value, and mitochondrial membrane potential in stored platelets (as compared to non-LLL-treated control platelets stored under similar conditions). These much improved conditions of stored platelets concurred with increasing platelet counts and diminished ROS production. The following experimental results are shown for the purpose of illustration only and are not intended to limit the scope of the appended claims.

Figure 18:
FIG. 18 is an experimental result showing that LLL increases ATP synthesis in fresh platelets.

As shown in FIG. 18, LLL increases ATP synthesis in fresh platelets. Platelet-rich plasma (PRP) were prepared from 8-week-old C57BL/6 mice, and illuminated with an 808-nm LED at 10 mW/cm². As shown in chart 158, ATP synthesis in platelets was enhanced significantly by LLL at energy densities from 0.5 J/cm² to 10 J/cm². n=6, *p<0.05, p<0.01, *p<0.001, ns, not significant.

Figure 19:
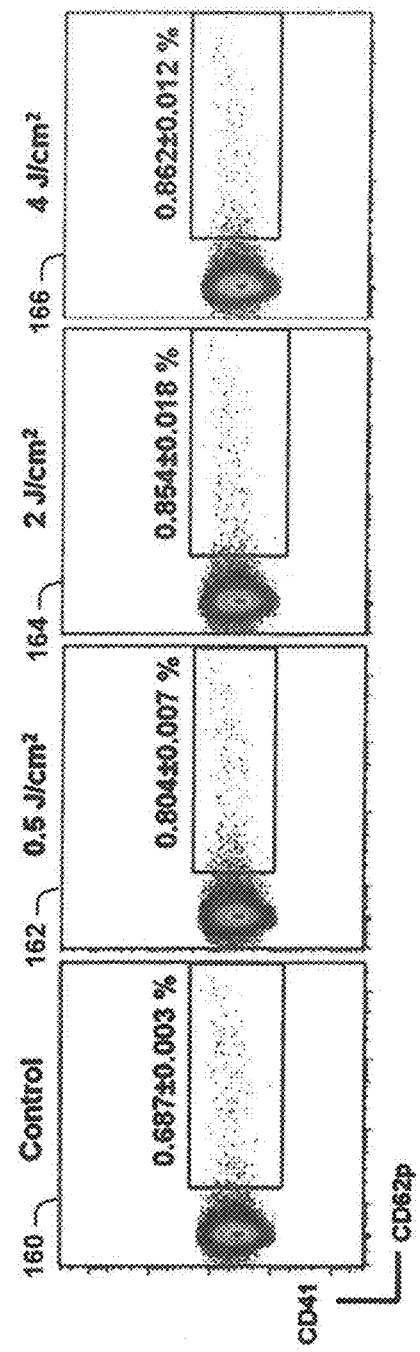
FIG. 19 is an experimental result showing that LLL does not activate platelets.

As shown in FIG. 19, LLL does not activate platelets. Platelet storage is often associated with platelet activation that reduces efficacy of transfusion and should be avoided. To corroborate that LLL doesn't activate platelets, PRP illuminated by various doses of LLL (diagrams 162, 164, 166) and non-treated control (diagram 160) were stained with platelet marker CD41 and activation biomarker CD62p. LLL at energy densities from 0.5 J/cm² to 4 J/cm² did not affect platelet activation (p>0.05).

Figure 20:
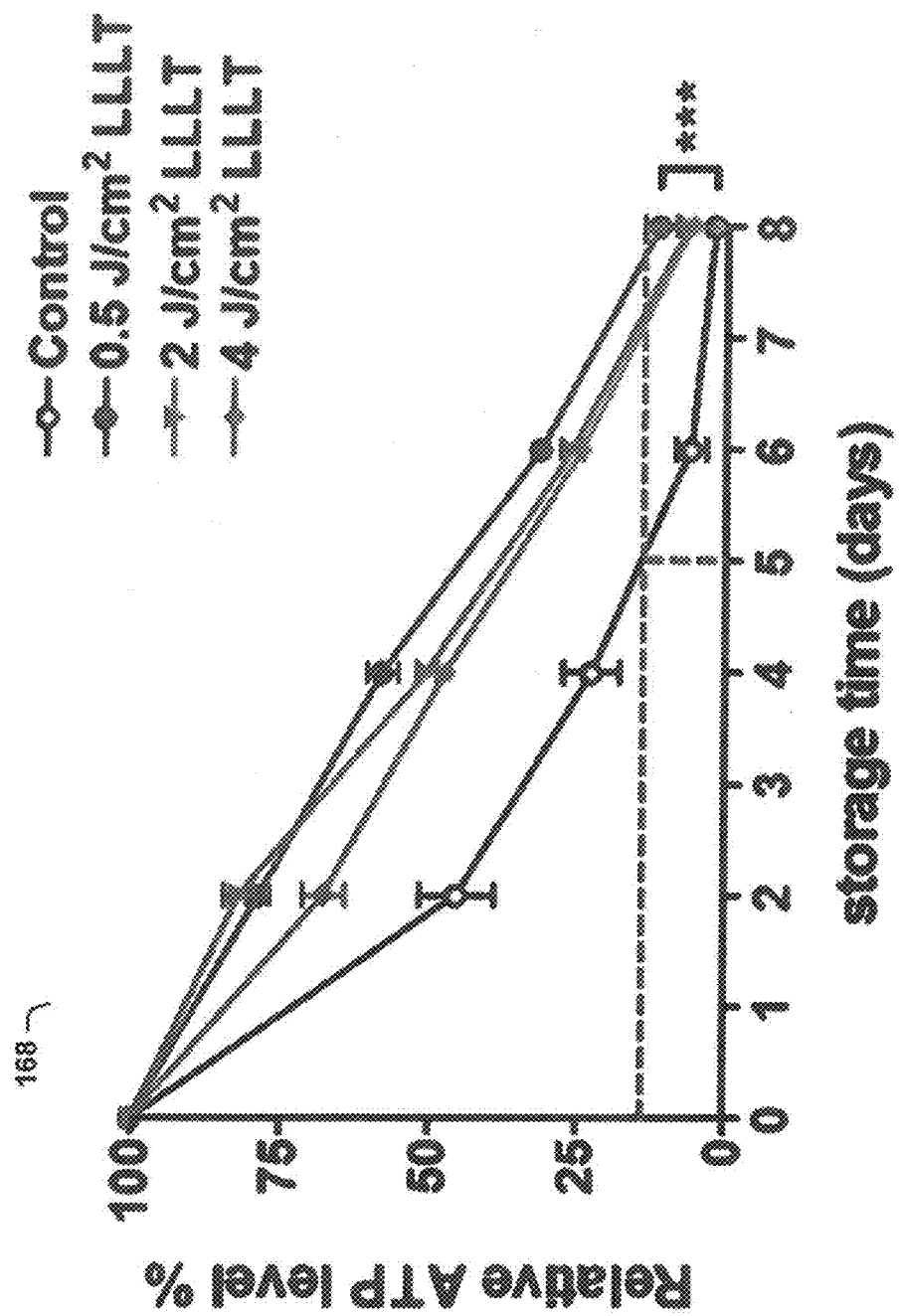
FIG. 20 is an experimental result showing that LLL significantly sustains ATP synthesis during platelet storage.

As shown in FIG. 20, LLL significantly sustains ATP synthesis during platelet storage. Platelet storage-associated mitochondrial injury reduces ATP production over time during storage. To determine whether LLL could sustain mitochondrial function during storage, murine PRP was prepared from 8-week-old C57BL/6 mice and stored for 8 days in a standard condition (22° C. with constant flatbed agitation at 70 cycles per minute). LLL was administered only once at 1 hr after PRP collection at an energy density of 0.5, 2 or 4 J/cm². ATP levels were determined every other day during storage. As shown in graph 168, ATP levels in PRP treated with LLL at 0.5, 2 or 4 J/cm² were significantly higher than control at all times tested. Importantly, the ATP level in 8-day-stored platelets treated with 0.5 J/cm² LLL was similar to that measured in 5-day stored platelets. The latter is a standard time of current platelet storage and the result clearly suggests a great potential to extend a platelet storage time to 8 days from 5 days. n=6, ***p<0.001, compared to non-treated control.

Figure 21:
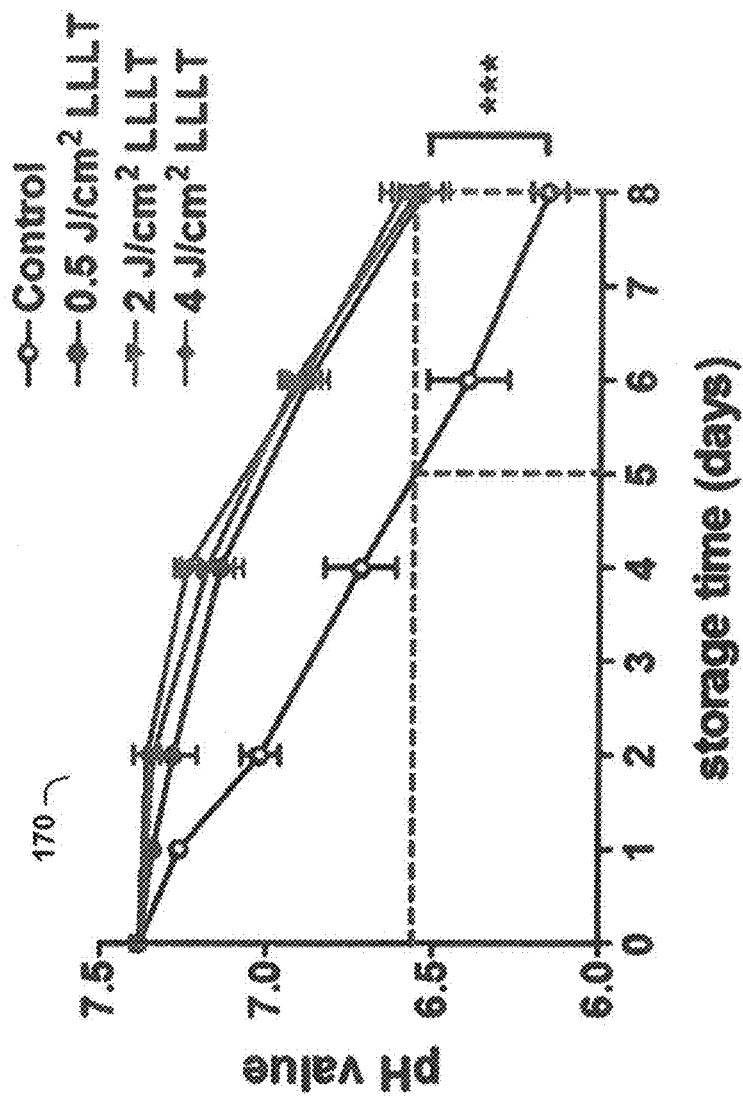
FIG. 21 is an experimental result showing LLL significantly blunts the decrease in the pH value of stored platelets over time.

As shown in FIG. 21, LLL significantly blunts a decrease in pH value in stored platelets (e.g., murine PRP). Murine PRP was prepared and treated with LLL similarly to the data shown in FIG. 20. pH values of each sample were determined every other day during storage. As shown in graph 170, LLL significantly retains pH values over controls during the 8 days of platelet storage. On day 8 of storage, platelets treated with LLL at all energy densities tested had a pH value as same as that in non-treated PRP stored for 5 days under similar conditions. n=6, ***p<0.001, compared to non-treated control.

Figure 22:
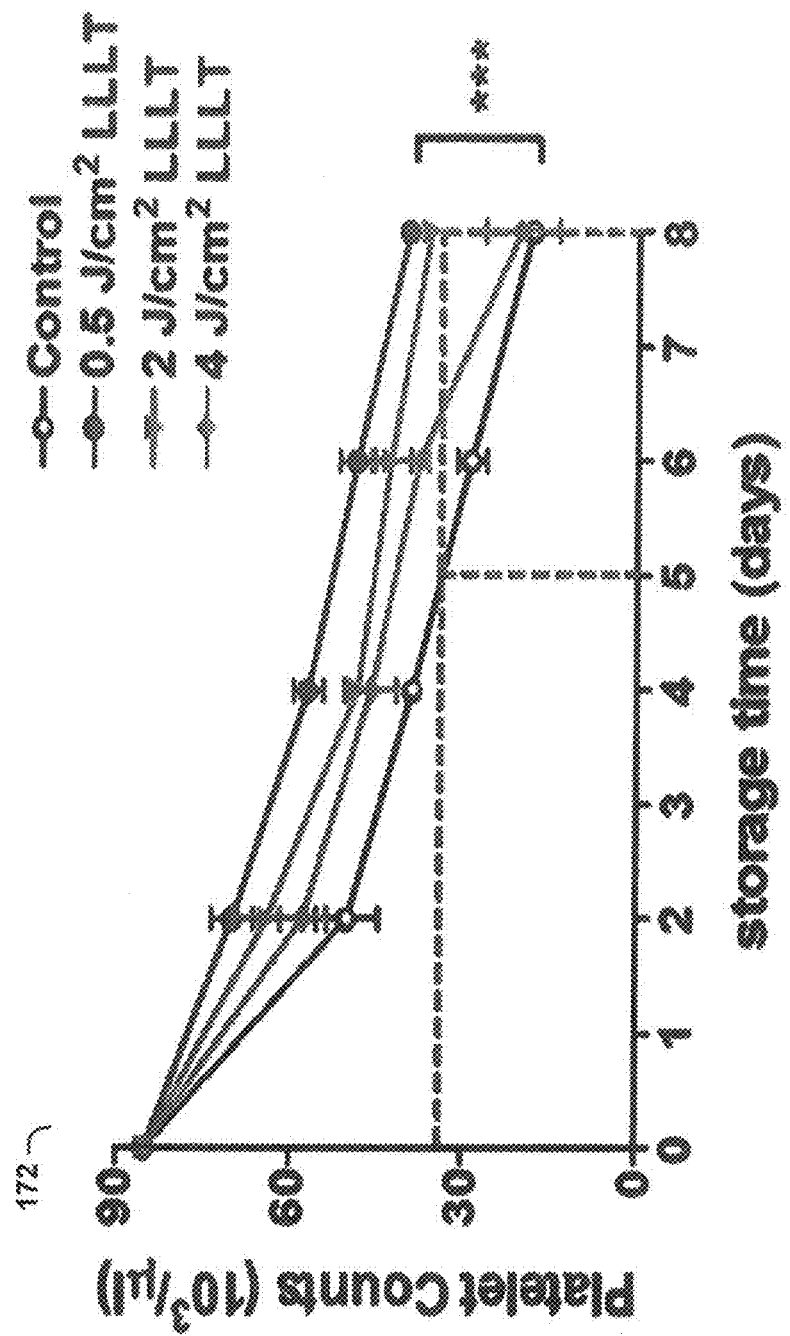
FIG. 22 is an experimental result showing that LLL significantly improves viability of stored platelets.

As shown in FIG. 22 LLL significantly improves the viability of stored platelets. Murine PRP was prepared and treated with LLL similarly to the data shown in FIG. 20. Consistent with great improvement of energy metabolism, graph 172 illustrates that platelet counts were significantly higher with LLL treatment at 0.5 or 2 J/cm² than non-treated control at all time points. Once again, platelet counts on day 8 of the storage with 0.5 or 2 J/cm² LLL were similar as those platelets stored for 5 days in the absence of LLL. LLL at 4 J/cm² appeared to have relatively less effect on platelet viability as compared to 0.5 or 2 J/cm², in 8-day-storage. n=6, ***p<0.001, compared to non-treated control.

Figure 23:
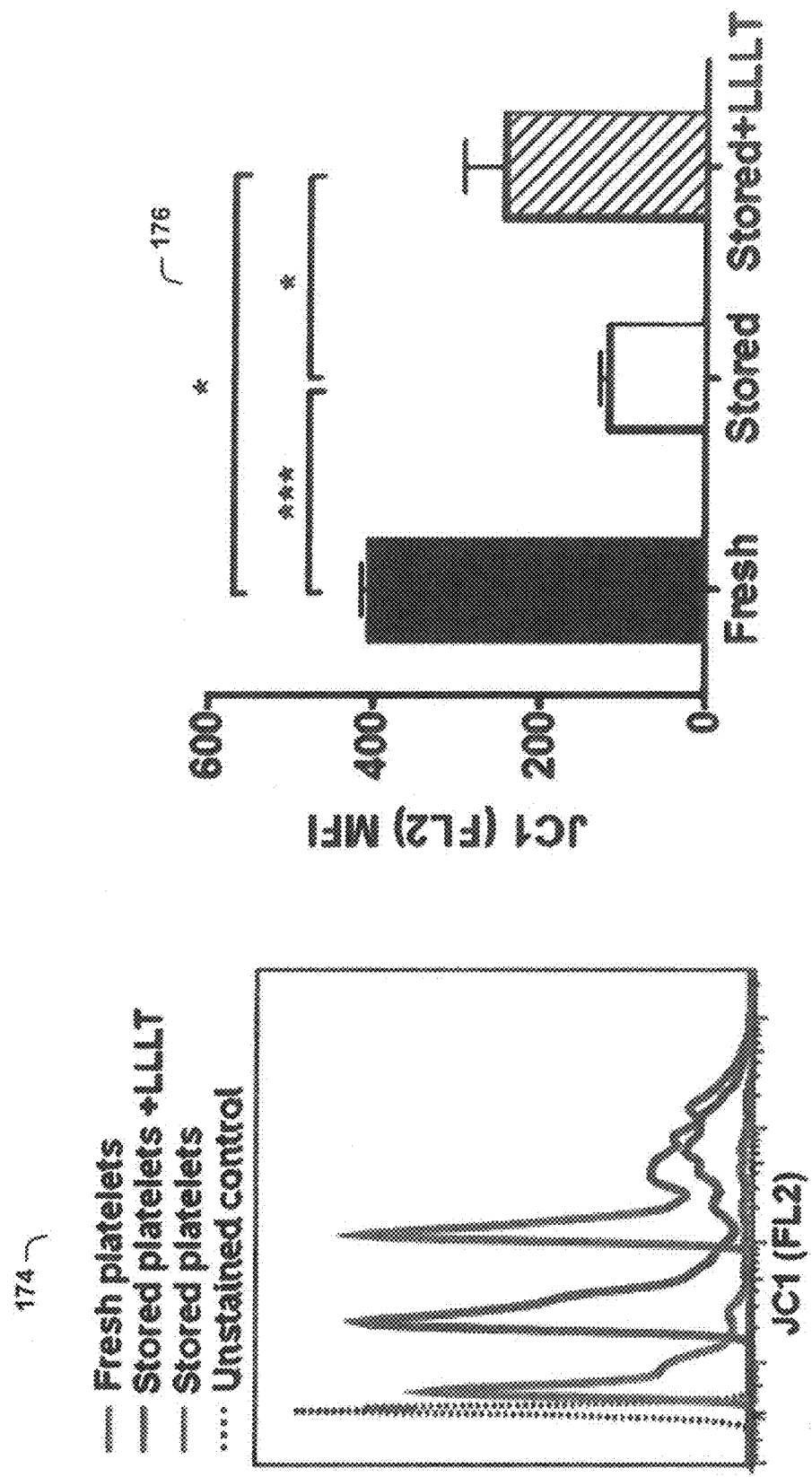
FIG. 23 is an experimental result showing that LLL significantly sustains mitochondrial membrane potential of stored platelets.

As shown in FIG. 23, LLL significantly sustains mitochondrial membrane potential of stored platelets. Murine PRP was prepared d from 8-week-old C57BL/6 mice and stored as above. A single dose of 0.5 J/cm² LLL was administered at 1 hr after PRP collection. Changes of mitochondrial membrane potential were determined by fluorochrome dye JC1 in platelets stored for 5 days. As shown in graph 174 and chart 176, compared to fresh platelets (Fresh), stored platelets showed a dramatic decline of mitochondrial membrane potential (stored), which was the major adverse event occurring during platelet storage. However, LLL significantly retained mitochondrial membrane potential of stored platelets (Stored+LLL). n=6, *p<0.05, p<0.01, *p<0.001.

Figure 24:
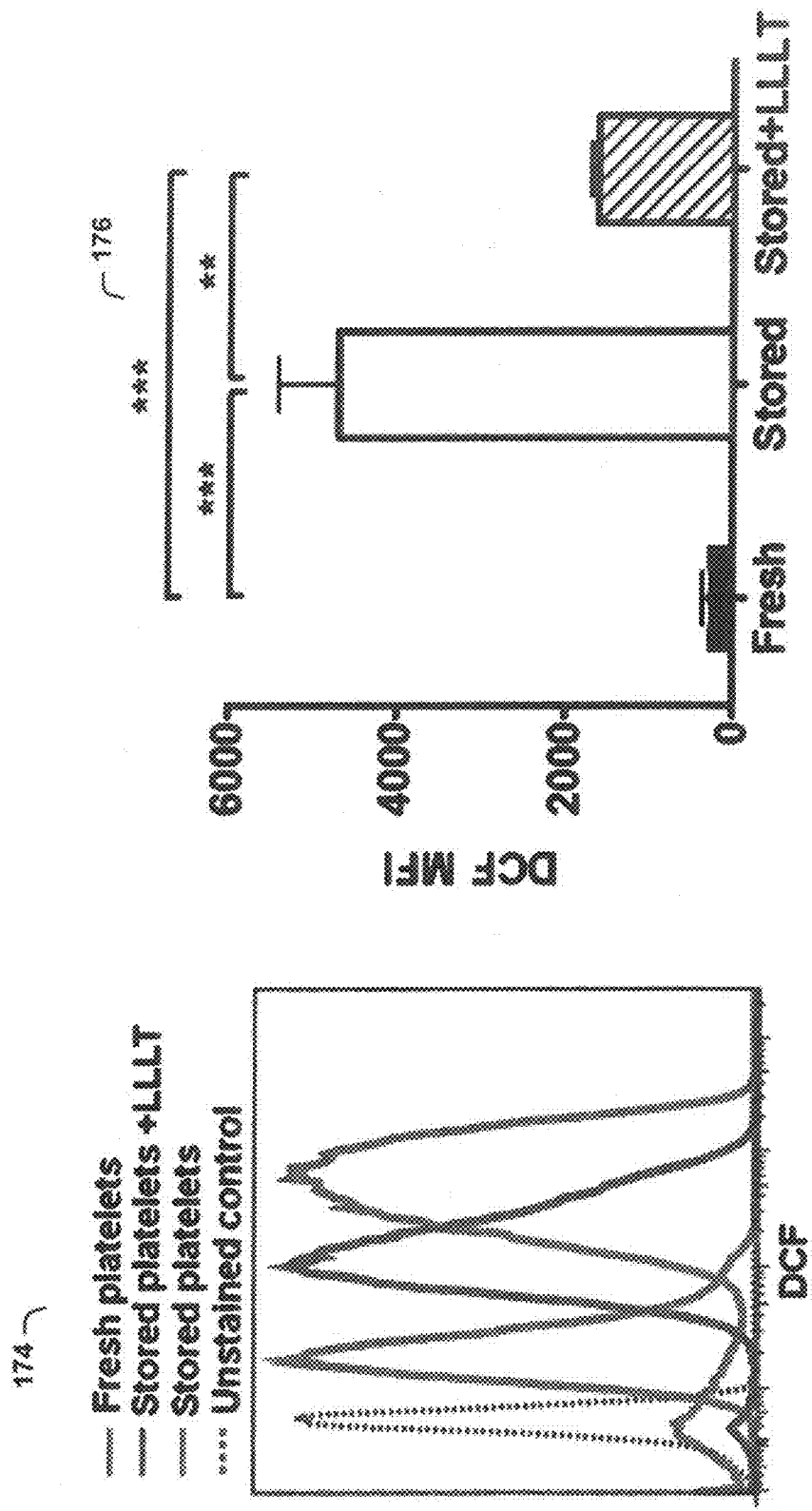
FIG. 24 is an experimental result showing that LLL reduces the production of reactive oxygen species (ROS) during platelet storage.

As shown in FIG. 24, LLL reduces the production of reactive oxygen species (ROS) during platelet storage. Increased ROS production secondarily to mitochondrial injury can damage platelets and mitochondria, reducing the viability of stored platelets. To determine the effect of LLL on ROS production during platelet storage, murine PRP was stored similarly to the data shown in FIG. 20. ROS levels were determined by cell-permeant fluorescent dye, 2',7'-dichlorodihydrofluorescein diacetate (H2DCFDA) (also known as dichlorofluores cin diacetate or DCF) in platelets stored for 5 days. As shown in graph 174 and chart 176, a significant reduction of ROS formation was found in platelets treated with a single dose of 0.5 J/cm² LLL before storage. n=6, p<0.01, *p<0.001.

From the above description, those skilled in the art will perceive improvements, changes and modifications. Such improvements, changes and modifications are within the skill of one in the art and are intended to be covered by the appended claims.

What is claimed is:

1. A method for enhancing platelet biogenesis comprising:
    applying low level light (LLL) transcutaneously to at least one platelet-making bone, wherein the LLL has an power density at the at least one platelet-making bone of from 0.1 mW/cm² to 50 mW/cm², wherein a surface power density of the LLL is higher than the power density at the at least one platelet-making bone and based on skin pigmentation; and augmenting ATP synthesis by platelet precursors in bone marrow of the at least one platelet-making bone to facilitate platelet biogenesis;
wherein the LLL has an energy density at the at least one platelet-making bone of from 0.1 J/cm² to 0.5 J/cm².

2. The method of claim 1, wherein the LLL is delivered by one or more light emitting diodes.

3. The method of claim 1, further comprising administering one or more pharmaceutical treatments with the LLL.

4. The method of claim 3, wherein the one or more pharmaceutical treatments promote megakaryopoiesis.

5. The method of claim 4, wherein the parameters for the LLL comprise a fluence value density at the at least one platelet-making bone based on the skin pigmentation of the patient.

6. The method of claim 3, wherein the one or more pharmaceutical treatments enhance mitochondrial biogenesis and/or activity or improve mitochondrial function.

7. The method of claim 1, wherein the applying is controlled by a control signal,
wherein the control signal sets parameters for the LLL.

8. The method of claim 7, wherein the parameters for the LLL comprise at least two of on time, off time, and a wave characteristic.

9. The method of claim 8, wherein the wave characteristic is pulsed or continuous.

10. The method of claim 1, wherein the LLL penetrates into tissue at depths of from 3 cm to at least 13 cm.

11. The method of claim 10, wherein the LLL is provided by a super pulsed GaAs laser.

12. The method of claim 1, wherein the LLL is provided by a monochromatic laser or a light emitting diode, wherein the LLL has a wavelength from 600 nm to 1500 nm.

13. The method of claim 12, wherein the LLL has a wavelength of 808 nm, 810 nm or 980 nm.

14. The method of claim 1, wherein the augmenting the ATP synthesis occurs for at least 30 minutes post application of the LLL.

15. The method of claim 1, wherein the augmenting the ATP synthesis occurs for at least 1 hour post application of the LLL.

16. The method of claim 1, wherein the augmenting the ATP synthesis occurs for at least 1 day post application of the LLL.

17. The method of claim 1, wherein the platelet precursors comprise megakaryocytes.

18. The method of claim 1, wherein the platelet precursors comprise stem cells.

* * * * *

UNITED STATES PATENT AND TRADEMARK OFFICE
CERTIFICATE OF CORRECTION

PATENT NO. : 11,623,103 B2
APPLICATION NO. : 16/875111
DATED : April 11, 2023
INVENTOR(S) : Meixiong Wu et al.

It is certified that error appears in the above-identified patent and that said Letters Patent is hereby corrected as shown below:

In the Specification

Column 9, Line 20, "$\geq 3.5$ J/cm$^2$" should be --$\geq 0.5$ J/cm$^2$--.

Signed and Sealed this
Sixteenth Day of May, 2023

Katherine Kelly Vidal
*Director of the United States Patent and Trademark Office*